(12) United States Patent
Nott et al.

(10) Patent No.: US 11,497,546 B2
(45) Date of Patent: Nov. 15, 2022

(54) AREA RATIOS OF PATTERNED COATINGS ON RF ELECTRODES TO REDUCE STICKING

(71) Applicant: Cilag GmbH International, Zug (CH)

(72) Inventors: Cameron R. Nott, Fairfield, OH (US); Gregory A. Trees, Loveland, OH (US)

(73) Assignee: Cilag GmbH International, Zug (CH)

( * ) Notice: Subject to any disclaimer, the term of this patent is extended or adjusted under 35 U.S.C. 154(b) by 761 days.

(21) Appl. No.: 15/476,665

(22) Filed: Mar. 31, 2017

(65) Prior Publication Data

US 2018/0280075 A1 Oct. 4, 2018

(51) Int. Cl.
*A61B 18/14* (2006.01)
*A61B 18/00* (2006.01)
(Continued)

(52) U.S. Cl.
CPC ... *A61B 18/1445* (2013.01); *A61B 2017/00849* (2013.01); *A61B 2017/00929* (2013.01); *A61B 2018/0013* (2013.01); *A61B 2018/0063* (2013.01); *A61B 2018/00083* (2013.01); *A61B 2018/00107* (2013.01);
(Continued)

(58) Field of Classification Search
CPC .. A61B 2017/00831; A61B 2017/0084; A61B 2017/00849; A61B 2017/00853; A61B 2017/00929; A61B 2018/00059; A61B 2018/00083; A61B 2018/00107; A61B 2018/0013; A61B 2018/00607;
(Continued)

(56) References Cited

U.S. PATENT DOCUMENTS 2,366,274 A 1/1945 Luth et al.
2,458,152 A 1/1949 Eakins
(Continued)

FOREIGN PATENT DOCUMENTS

CN 1634601 A 7/2005
CN 1922563 A 2/2007
(Continued)

OTHER PUBLICATIONS

Abbott, et al. Proceedings of the 2007 IEEEIRDJ International Conference on Intelligent Robots and Systems. 410-416, 2007.
(Continued)

*Primary Examiner* — Daniel W Fowler
*Assistant Examiner* — Bradford C. Blaise

(57) ABSTRACT

An electrosurgical system includes an RF current generator, a handle body, and an end effector. The end effector may include a first and a second energy delivery surface. At least a portion of either first or second energy delivery surfaces, or both, may include one or more patterned coatings of an electrically non-conducting non-stick material. The material may be deposited on a surface of, within a depression in, or on features extending from the energy surfaces, or through an overmolding process. The patterned coating may be formed from a coating of the material from which portions have been removed. An energy delivery surface has a first area, and the patterned coating has a second area. A ratio of the second area to the first area may be less than or equal to about 0.9, less than or equal to about 0.7, or less than or equal to about 0.5.

10 Claims, 16 Drawing Sheets

(51) Int. Cl.
*A61B 18/12* (2006.01)
*A61B 17/00* (2006.01)

(52) U.S. Cl.
CPC .............. *A61B 2018/00607* (2013.01); *A61B 2018/126* (2013.01); *A61B 2018/1455* (2013.01)

(58) Field of Classification Search
CPC ...... A61B 2018/0063; A61B 2018/126; A61B 2018/1455; A61B 18/1445
See application file for complete search history.

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |

(56) References Cited

U.S. PATENT DOCUMENTS

| | | |
|---|---|---|
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,307 A | 4/1997 | Donlon et al. |
| 5,618,492 A | 4/1997 | Auten et al. |
| 5,624,452 A | 4/1997 | Yates |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |

(56) References Cited

U.S. PATENT DOCUMENTS

| | | |
|---|---|---|
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A * | 4/1999 | Eggers ............ A61B 18/1442 606/51 |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,093,186 A | 7/2000 | Goble |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,193,709 B1 | 2/2001 | Miyawaki et al. |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,228,084 B1 | 5/2001 | Kirwan, Jr. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| 6,379,351 B1 | 4/2002 | Thapliyal et al. |
| D457,958 S | 5/2002 | Dycus et al. |
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |

(56) References Cited

U.S. PATENT DOCUMENTS

| | | |
|---|---|---|
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Muller et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,696,844 B2 | 2/2004 | Wong et al. |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,723,094 B1 | 4/2004 | Desinger |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Safer |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |

(56) References Cited

U.S. PATENT DOCUMENTS

| | | |
|---|---|---|
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,147,650 B2 | 12/2006 | Lee |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Ratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,658 B2 | 9/2007 | Woloszko et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,048 B2 | 10/2007 | Goble et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,344,533 B2 | 3/2008 | Pearson et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckal et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |
| 7,488,319 B2 | 2/2009 | Yates |

(56) References Cited

U.S. PATENT DOCUMENTS

| | | |
|---|---|---|
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,608,083 B2 | 10/2009 | Lee et al. |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,069 B1 | 3/2010 | Baker et al. |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,887,535 B2 | 2/2011 | Lands et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,947,039 B2 | 5/2011 | Sartor |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |

(56) References Cited

U.S. PATENT DOCUMENTS

| | | |
|---|---|---|
| 7,981,113 B2 | 7/2011 | Truckai et al. |
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,940 B2 | 4/2012 | Johnson et al. |
| 8,177,784 B2 | 5/2012 | Van Wyk et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,221,416 B2 | 7/2012 | Townsend |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,398,633 B2 | 3/2013 | Mueller |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,911 B2 | 5/2013 | Mueller |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |

(56) References Cited

U.S. PATENT DOCUMENTS

| | | |
|---|---|---|
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,807,414 B2 | 8/2014 | Ross et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,012 B2 | 12/2014 | Conley et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,414 B2 | 12/2014 | Stone et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,332 B2 | 3/2015 | Farritor et al. |
| 8,974,453 B2 | 3/2015 | Wang |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,520 B2 | 3/2015 | Van Wyk et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,023,035 B2 | 5/2015 | Allen, IV et al. |

(56) References Cited

U.S. PATENT DOCUMENTS

| | | |
|---|---|---|
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,113 B2 | 6/2015 | Bloom et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,082 B2 | 10/2015 | Evans et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,061 B2 | 6/2016 | Plascencia, Jr. et al. |
| 9,358,065 B2 | 6/2016 | Ladtkow et al. |
| 9,364,225 B2 | 6/2016 | Sniffin et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,468,490 B2 | 10/2016 | Twomey et al. |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,489 B2 | 7/2017 | Woloszko et al. |
| 9,713,491 B2 | 7/2017 | Roy et al. |
| 9,724,118 B2 | 8/2017 | Schulte et al. |
| 9,724,152 B2 | 8/2017 | Horiie et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,775,665 B2 | 10/2017 | Ellman |
| 9,775,669 B2 | 10/2017 | Marczyk et al. |
| 9,782,214 B2 | 10/2017 | Houser et al. |
| 9,782,220 B2 | 10/2017 | Mark et al. |
| 9,788,891 B2 | 10/2017 | Christian et al. |
| 9,795,436 B2 | 10/2017 | Yates et al. |
| 9,802,033 B2 | 10/2017 | Hibner et al. |

(56) References Cited

U.S. PATENT DOCUMENTS

| | | |
|---|---|---|
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,954 B2 | 2/2018 | Van Wyk et al. |
| 9,888,958 B2 | 2/2018 | Evans et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,918,773 B2 | 3/2018 | Ishikawa et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,034,707 B2 | 7/2018 | Papaioannou et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,135,242 B2 | 11/2018 | Baber et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,231,776 B2 | 3/2019 | Artale et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,307,203 B2 | 6/2019 | Wyatt |
| 10,314,638 B2 | 6/2019 | Gee et al. |
| 10,321,950 B2 | 6/2019 | Yates et al. |
| 10,342,602 B2 | 7/2019 | Strobl et al. |
| 10,413,352 B2 | 9/2019 | Thomas et al. |
| 10,420,601 B2 | 9/2019 | Marion et al. |
| 10,420,607 B2 | 9/2019 | Woloszko et al. |
| 10,426,873 B2 | 10/2019 | Schultz |
| 10,433,900 B2 | 10/2019 | Harris et al. |
| 10,441,345 B2 | 10/2019 | Aldridge et al. |
| 10,463,421 B2 | 11/2019 | Boudreaux et al. |
| 10,478,243 B2 | 11/2019 | Couture et al. |
| 10,485,607 B2 | 11/2019 | Strobl et al. |
| 10,524,852 B1 | 1/2020 | Cagle et al. |
| 10,524,854 B2 | 1/2020 | Woodruff et al. |
| 10,675,082 B2 | 6/2020 | Shelton, IV et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0133149 A1 | 9/2002 | Bessette |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144660 A1 | 7/2003 | Mollenauer |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0122423 A1* | 6/2004 | Dycus .................. A61B 90/03 606/51 |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0106379 A1 | 5/2006 | O'Brien et al. |
| 2006/0159731 A1 | 7/2006 | Shoshan |
| 2006/0190034 A1 | 8/2006 | Nishizawa et al. |
| 2006/0211943 A1 | 9/2006 | Beaupre |

(56) References Cited

U.S. PATENT DOCUMENTS

| | | |
|---|---|---|
| 2006/0253050 A1 | 11/2006 | Yoshimine et al. |
| 2006/0270916 A1 | 11/2006 | Skwarek et al. |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0032785 A1 | 2/2007 | Diederich et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0103495 A1 | 5/2008 | Mihori et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0228179 A1 | 9/2008 | Eder et al. |
| 2008/0234709 A1 | 9/2008 | Houser |
| 2008/0281200 A1 | 11/2008 | Voic et al. |
| 2008/0281315 A1 | 11/2008 | Gines |
| 2008/0287948 A1 | 11/2008 | Newton et al. |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0114701 A1 | 5/2009 | Zemlok et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0264879 A1 | 10/2009 | Mcclurken et al. |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0022824 A1 | 1/2010 | Cybulski et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0087224 A1 | 4/2011 | Cadeddu et al. |
| 2011/0118601 A1 | 5/2011 | Barnes et al. |
| 2011/0125151 A1 | 5/2011 | Strauss et al. |
| 2011/0257680 A1 | 10/2011 | Reschke et al. |
| 2011/0270245 A1 | 11/2011 | Horner et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0078244 A1 | 3/2012 | Worrell et al. |
| 2012/0080334 A1 | 4/2012 | Shelton, IV et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0190753 A1 | 7/2013 | Garrison et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0039493 A1 | 2/2014 | Conley et al. |
| 2014/0131419 A1 | 5/2014 | Bettuchi |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263541 A1 | 9/2014 | Leimbach et al. |
| 2014/0263552 A1 | 9/2014 | Hall et al. |
| 2014/0350540 A1 | 11/2014 | Kitagawa et al. |
| 2015/0032150 A1 | 1/2015 | Ishida et al. |
| 2015/0080876 A1 | 3/2015 | Worrell et al. |
| 2015/0250531 A1 | 9/2015 | Dycus et al. |
| 2015/0257819 A1 | 9/2015 | Dycus et al. |
| 2015/0272571 A1 | 10/2015 | Leimbach et al. |
| 2015/0272659 A1 | 10/2015 | Boudreaux et al. |
| 2015/0327918 A1 | 11/2015 | Sobajima et al. |
| 2016/0045248 A1 | 2/2016 | Unger et al. |

(56) References Cited

U.S. PATENT DOCUMENTS

| | | |
|---|---|---|
| 2016/0051316 A1 | 2/2016 | Boudreaux |
| 2016/0066980 A1 | 3/2016 | Schall et al. |
| 2016/0100747 A1 | 4/2016 | Nitsan et al. |
| 2016/0143687 A1 | 5/2016 | Hart et al. |
| 2016/0157923 A1 | 6/2016 | Ding |
| 2016/0157927 A1 | 6/2016 | Corbett et al. |
| 2016/0175029 A1 | 6/2016 | Witt et al. |
| 2016/0199124 A1 | 7/2016 | Thomas et al. |
| 2016/0199125 A1 | 7/2016 | Jones |
| 2016/0270780 A1 | 9/2016 | Hall et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296270 A1 | 10/2016 | Strobl et al. |
| 2017/0056097 A1 | 3/2017 | Monson et al. |
| 2017/0105786 A1 | 4/2017 | Scheib et al. |
| 2017/0105787 A1 | 4/2017 | Witt et al. |
| 2017/0105789 A1 | 4/2017 | Boudreaux et al. |
| 2017/0135751 A1 | 5/2017 | Rothweiler et al. |
| 2017/0164972 A1 | 6/2017 | Johnson et al. |
| 2017/0189102 A1 | 7/2017 | Hibner et al. |
| 2017/0312014 A1 | 11/2017 | Strobl et al. |
| 2017/0312015 A1 | 11/2017 | Worrell et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0325878 A1 | 11/2017 | Messerly et al. |
| 2017/0325886 A1 | 11/2017 | Graham et al. |
| 2017/0367751 A1 | 12/2017 | Ruddenklau et al. |
| 2018/0085156 A1 | 3/2018 | Witt et al. |
| 2018/0125571 A1 | 5/2018 | Witt et al. |
| 2018/0161034 A1 | 6/2018 | Scheib et al. |
| 2018/0228530 A1 | 8/2018 | Yates et al. |
| 2018/0235626 A1 | 8/2018 | Shelton, IV et al. |
| 2018/0263683 A1 | 9/2018 | Renner et al. |
| 2018/0368906 A1 | 12/2018 | Yates et al. |
| 2019/0000468 A1 | 1/2019 | Adams et al. |
| 2019/0000470 A1 | 1/2019 | Yates et al. |
| 2019/0000528 A1 | 1/2019 | Yates et al. |
| 2019/0000530 A1 | 1/2019 | Yates et al. |
| 2019/0000536 A1 | 1/2019 | Yates et al. |
| 2019/0000555 A1 | 1/2019 | Schings et al. |
| 2019/0059980 A1 | 2/2019 | Shelton, IV et al. |
| 2019/0099209 A1 | 4/2019 | Witt et al. |
| 2019/0099212 A1 | 4/2019 | Davison et al. |
| 2019/0099213 A1 | 4/2019 | Witt et al. |
| 2019/0099217 A1 | 4/2019 | Witt et al. |
| 2019/0200998 A1 | 7/2019 | Shelton, IV et al. |
| 2019/0314015 A1 | 10/2019 | Shelton, IV et al. |
| 2020/0375651 A1 | 12/2020 | Witt et al. |
| 2021/0100605 A1 | 4/2021 | Renner et al. |
| 2021/0338309 A1 | 11/2021 | Witt et al. |

FOREIGN PATENT DOCUMENTS

| | | |
|---|---|---|
| CN | 2868227 Y | 2/2007 |
| DE | 4300307 A1 | 7/1994 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| ES | 2419159 A2 | 8/2013 |
| GB | 2032221 A | 4/1980 |
| JP | H08229050 A | 9/1996 |
| JP | 2002186627 A | 7/2002 |
| JP | 2009213878 A | 9/2009 |
| JP | 2010057926 A | 3/2010 |
| JP | 2012019846 A | 2/2012 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |
| WO | WO-2012061638 A1 | 5/2012 |
| WO | WO-2013131823 A1 | 9/2013 |
| WO | WO-2016088017 A1 | 6/2016 |

OTHER PUBLICATIONS

Cadeddu et al., "Magnetic positioning system for trocarless laparoscopic instruments," American College of Surgeons Poster, 2004.

Cadeddu et al., "Novel magnetically guided intra-abdominal camera to facilitate laparoendoscopic single site surgery: initial human experience," Surgical Endoscopy, SAGES Oral Manuscript, 2009.

Cadeddu et al., "Transabdominal magnetic anchoring system for trocar-less laparoscopic surgery," American Urological Association Poster, 2002.

Cadeddu et al., "Transabdominal magnetic anchoring system for trocar-less laparoscopic surgery," Journal of Urology Abstract, 2002.

Castellvi et al., "Completely transvaginal NOTES cholecystectomy in a porcine model using novel endoscopic instrumentation," Accepted for Poster Presentation, SAGES Annual Meeting, 2009.

Castellvi et al., "Hybrid transgastric NOTES cholecystectomy in a porcine model using a magnetically anchored cautery and novel instrumentation," Submitted for Presentation, ASGE, 2009.

Castellvi et al., "Hybrid transvaginal NOTES sleeve gastrectomy in a porcine model using a magnetically anchored camera and novel instrumentation," Accepted for Poster Presentation, SAGES Annual Meeting, 2009.

Duchene et al., "Magnetic positioning system for trocarless laparoscopic instruments," Engineering and Urology Society Poster, 2004.

Fernandez et al., "Development of a transabdominal anchoring system for trocar-less laparoscopic surgery," ASME Proceedings of/MECE, 2003.

Gedeon et al., "Maximizing coupling strength of magnetically anchored notes instruments: How thick can we go?" Submittedfor Presentation, Poster, SAGES Annual Meeting, 2008.

Gedeon et al., "Maximizing coupling strength of magnetically anchored notes instruments: How thick can we go?" SAGES Annual Meeting Poster, 2008.

Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.

Peirs et al., "A miniature manipulator for integration in self-propelling endoscope," Sensors and Actuators, 92:343-9, 2001.

Raman et al., "Complete transvaginal NOTES nephrectomy using magnetically anchored instrumentation," Journal of Endourology, 23(3):, 2009.367-371,2009.

Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.

Scott et al., "A randomized comparison of laparoscopic, flexible endoscopic, and wired and wireless magnetic NOTES cameras on ex-vivo and in-vivo surgical performance," Digestive Disease Week (DDW), American Society for Gastrointestinal Endoscopy (ASGE) Annual Meeting Abstract, 2008.

Scott et al., "Completely transvaginal NOTES cholecystectomy using magnetically anchored instruments," Surg. Endosc., 21:2308-2316, 2007.

(56) References Cited

OTHER PUBLICATIONS

Scott et al., "Evaluation of a novel air seal access port for transvaginal notes cholecystectomy," Submitted for Presentation, SAGES Annual Meeting, 2008.
Scott et al., "Magnetically anchored instruments for transgastric endoscopic surgery," Oral Presentation for SAGES Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Trans gastric, transcolonic, and transvaginal cholecystectomy using magnetically anchored instruments," SAGES Annual Meeting Poster, 2007.
Scott et al., "Transvaginal single access 'pure' NOTES sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' NOTES procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for NOTES," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Weir, C.E., "Rate of shrinkage of tendon collagen - heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Meeh. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Sullivan, "Cost-Constrained Selection of Strand Diameter and No. in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
Leonard I. Malis, M.D., "The Value of Irrigation During Bipolar Coagulation," 1989.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al., "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23,

(56) References Cited

OTHER PUBLICATIONS

2008], Retrieved from the internet: URL: http//wonder.cdc.gov/wonder/prevguid/p0000191/p0000191 .asp (15 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Hörmann et al., "Reversible and irreversible denaturation of collagen fibers." Biochemistry, 10, pp. 932-937 (1971).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

\* cited by examiner

AREA RATIOS OF PATTERNED COATINGS ON RF ELECTRODES TO REDUCE STICKING

BACKGROUND

Electrosurgical devices are used in many surgical operations. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar operation. During bipolar operation, current is introduced into and returned from the tissue by active and return electrodes, respectively, of the end effector. Bipolar devices may also have an end effector consisting of two or more jaws each having at least one of the active and or return electrodes. At least one of the jaws is moveable from a position spaced apart from the opposing jaw for receiving tissues to a position in which the space between the jaws is less than that of the first position. Movement of the moveable jaw compresses the tissue held between. Heat generated by the current flow through the tissue in combination with the compression achieved by the jaw movement may form hemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrosurgical devices also may include mechanisms to clamp tissue together, such as a stapling device, and/or mechanisms to sever tissue, such as a tissue knife. The electrosurgical device may also include an ultrasonic vibrating blade. An electrosurgical device may include a shaft for placing the end effector proximate to tissue undergoing treatment. The shaft may be straight or curved, bendable or non-bendable. In an electrosurgical device including a straight and bendable shaft, the shaft may have one or more articulation joints to permit controlled bending of the shaft. Such joints may permit a user of the electrosurgical device to place the end effector in contact with tissue at an angle to the shaft when the tissue being treated is not readily accessible using an electrosurgical device having a straight, non-bending shaft.

Electrical energy applied by an electrosurgical device can be transmitted to the instrument by a generator. The electrical energy may be in the form of radio frequency ("RF") energy. The electrical energy may be in the form of radio frequency ("RF") energy that may be in a frequency range described in EN 60601-2-2:2009+A11:2011, Definition 201.3.218—HIGH FREQUENCY. For example, the frequency in monopolar RF applications is typically restricted to less than 5 MHz. However, in bipolar RF applications, the frequency can be almost anything. Frequencies above 200 kHz can be typically used for monopolar applications in order to avoid the unwanted stimulation of nerves and muscles which would result from the use of low frequency current. Lower frequencies may be used for bipolar techniques if the risk analysis shows the possibility of neuromuscular stimulation has been mitigated to an acceptable level. Normally, frequencies above 5 MHz are not used in order to minimize the problems associated with high frequency leakage currents. However, higher frequencies may be used in the case of bipolar techniques.

During its operation, an electrosurgical device can transmit RF energy through tissue compressed between the two or more jaws. Such RF energy may cause ionic agitation in the tissue, in effect producing resistive (joule) heating, and thereby increasing the temperature of the tissue. The temperatures involved during the sealing process may lead to tissue sticking to a stainless steel electrode. RF energy may work particularly well on connective and vascular tissue, which primarily comprise collagen and elastin that liquefies when heated and reforms into a fused mass when it cools. Because a distinct thermal spread boundary may be created between the affected tissue and the surrounding tissue, surgeons can operate with a high level of precision and control, without sacrificing un-targeted adjacent tissue. In many surgical procedures, RF energy may be useful for sealing blood vessels.

During surgical resection of tissue, blood vessels may be severed either as part of the procedure or ancillary to the resection of a tissue of interest. Once a blood vessel has been severed, blood may flow into the surgical site, potentially obscuring the site from view and rendering the surgical procedure more difficult. If the severed blood vessel is a major vessel, such as an artery or vein, the patient may suffer significant blood loss during the procedure thereby significantly compromising the patient's health.

It may be understood that successful electrosurgery-based sealing of a blood vessel requires the application of a sufficient compressive force to close the blood vessel, a consistent gap between electrodes, and the application of the RF energy to heat and seal the tissue under compression. In order to apply the sufficient compressive force to the blood vessel, the end effector jaws of the electrosurgical device must securely grasp the blood vessel and apply sufficient pressure to approximate the vessel's walls to a precise gap while the sealing process occurs.

It may be recognized that the application of the RF energy to heat and seal the tissue under compression may lead to changes in the tissue composition which may include charring or the forming of a coagulum from the heated tissue. The charred tissue or coagulum may adhere to one or more of the jaws of the end effector making it difficult to separate the sealed tissue from the end effector. In some circumstances, an attempt to manually separate the charred tissue or coagulum from the one or more jaws may result in a breach of the tissue seal, thereby permitting bleeding in the surgical site. Therefore, it may be useful to design an end effector of an electrosurgical device with components capable of allowing easy release of the sealed tissue from the one or more end effector jaws.

SUMMARY

In one aspect, an electrosurgical system may include an RF current generator, a handle body, and an end effector in mechanical communication with the handle body, in which the end effector may include a first jaw comprising a first energy delivery surface in electrical communication with a first terminal of the RF current generator, and a second jaw including a second energy delivery surface in electrical communication with a second terminal of the RF current generator, in which at least a portion of the first energy delivery surface includes a patterned coating of an electrically non-conducting non-stick material.

In one aspect of the electrosurgical system, the first energy delivery surface has a first area and the at least portion of the first energy delivery surface comprising the patterned coating has a second area.

In one aspect of the electrosurgical system, a ratio of the second area to the first area is less than or equal to about 0.9.

In one aspect of the electrosurgical system, a ratio of the second area to the first area is less than or equal to about 0.7.

In one aspect of the electrosurgical system, a ratio of the second area to the first area is less than or equal to about 0.5.

In one aspect of the electrosurgical system, the electrically non-conducting non-stick material has a surface energy value between 1100 mJ/m$^2$ and 5 mJ/m$^2$.

In one aspect of the electrosurgical system, the electrically non-conducting non-stick material has a surface energy value between 50 mJ/m$^2$ and 40 mJ/m$^2$.

In one aspect of the electrosurgical system, the electrically non-conducting non-stick material has a surface energy value between 40 mJ/m$^2$ and 12 mJ/m$^2$.

In one aspect, an end effector for an electrosurgical device may include a first jaw having a first energy delivery surface configured to be in electrical communication with a first terminal of an RF current generator, and a second jaw having a second energy delivery surface configured to be in electrical communication with a second terminal of the RF current generator, in which at least a portion of the first energy delivery surface includes a patterned coating of an electrically non-conducting non-stick material.

In one aspect of the end effector, the first energy delivery surface has a first area and the at least portion of the first energy delivery surface comprising the patterned coating has a second area.

In one aspect of the end effector, a ratio of the second area to the first area is less than or equal to about 0.8.

In one aspect of the end effector, a ratio of the second area to the first area is less than or equal to about 0.7.

In one aspect of the end effector, a ratio of the second area to the first area is less than or equal to about 0.5.

In one aspect of the end effector, the electrically non-conducting non-stick material has a surface energy value between 1100 mJ/m$^2$ and 5 mJ/m$^2$.

In one aspect of the end effector, the electrically non-conducting non-stick material has a surface energy value between 50 mJ/m$^2$ and 40 mJ/m$^2$.

In one aspect of the end effector, the electrically non-conducting non-stick material has a surface energy value between 40 mJ/m$^2$ and 12 mJ/m$^2$.

In one aspect of the end effector, the patterned coating includes the electrically non-conducting non-stick material disposed within one or more recessed features fabricated in the first energy delivery surface.

In one aspect of the end effector, the one or more recessed features include one or more circular features.

In one aspect of the end effector, the one or more recessed features include one or more rectangular features.

In one aspect of the end effector, the one or more recessed features include one or more linear features.

In one aspect of the end effector, the one or more linear features are disposed along or parallel to a longitudinal axis of the first energy delivery surface.

In one aspect of the end effector, the one or more linear features are disposed along or parallel to a transverse axis of the first energy delivery surface.

In one aspect of the end effector, the patterned coating includes the electrically non-conducting non-stick material disposed on and in direct physical communication with an exposed surface of the first energy delivery surface.

In one aspect of the end effector, the patterned coating includes a coating of the non-stick material lacking one or more portions of the non-stick material.

In one aspect of the end effector, the portions of the non-stick material include one or more circular portions of the non-stick material.

In one aspect of the end effector, the portions of the non-stick material include one or more rectangular portions of the non-stick material.

In one aspect of the end effector, the portions of the non-stick material include one or more elongated portions of the non-stick material.

In one aspect of the end effector, at least a portion of the second energy delivery surface includes a second patterned coating of the electrically non-conducting non-stick material that is disposed on and is in direct physical communication with an exposed surface of the second energy delivery surface; and in which the patterned coating is spatially offset with respect to the second patterned coating when the first jaw is brought into a proximate position to the second jaw.

In one aspect of the end effector, the second energy delivery surface has a third area and the at least portion of the second energy delivery surface comprising the second patterned coating has a fourth area.

In one aspect of the end effector, a ratio of the fourth area to the third area is less than or equal to about 0.8.

In one aspect of the end effector, a ratio of the fourth area to the third area is less than or equal to about 0.7.

In one aspect of the end effector, a ratio of the fourth area to the third area is less than or equal to about 0.6.

In one aspect of the end effector, the patterned coating includes a coating of the non-stick material lacking one or more elongated portions of the non-stick material and the second patterned coating comprises a coating of the non-stick material lacking one or more second elongated portions of the non-stick material.

BRIEF DESCRIPTION OF THE FIGURES

The features of the various aspects are set forth with particularity in the appended claims. The various aspects, however, both as to organization and methods of operation, together with advantages thereof, may best be understood by reference to the following description, taken in conjunction with the accompanying drawings as follows:

DETAILED DESCRIPTION

Figure 1A:
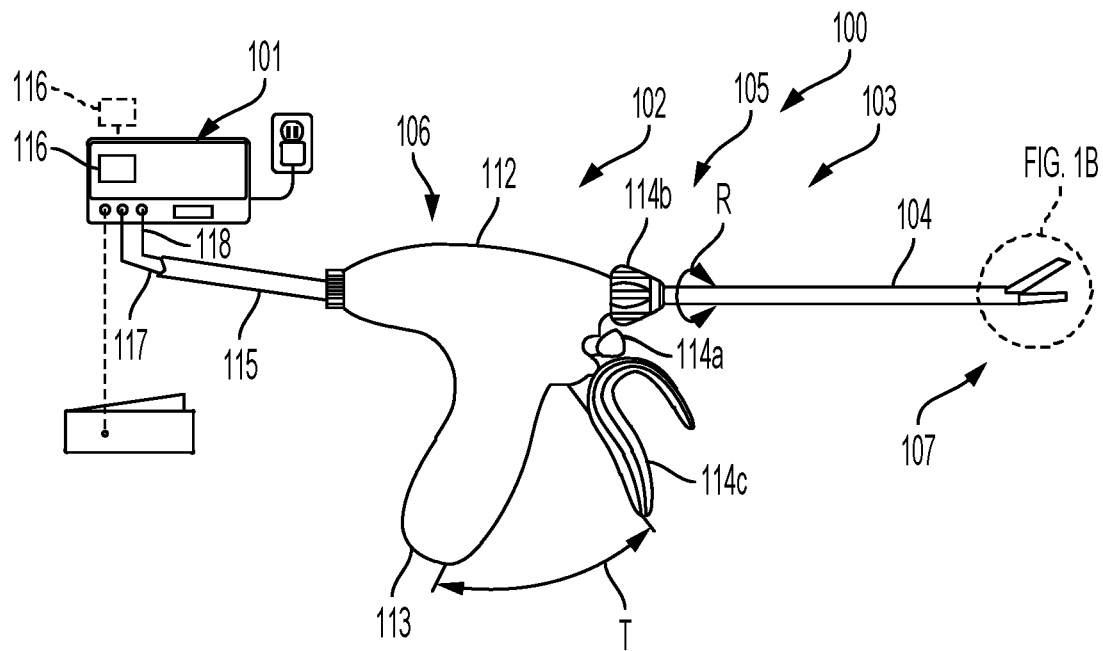
FIG. 1A shows a surgical instrument in electrical communication with an energy source, according to one aspect of the present disclosure.

The following description of certain examples of the technology should not be used to limit its scope. Other examples, features, aspects, aspects, and advantages of the technology will become apparent to those skilled in the art from the following description. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, aspects, examples, etc. described herein may be combined with any one or more of the other teachings, expressions, aspects, examples, etc. that are described herein. The following described teachings, expressions, aspects, examples, etc. should, therefore, not be viewed in isolation relative to each other. Various suitable ways in which the teachings herein may be combined will be readily apparent to those of ordinary skill in the art in view of the teachings herein. Such modifications and variations are intended to be included within the scope of the claims.

Also, in the following description, it is to be understood that terms such as front, back, inside, outside, upper, lower, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings. Throughout this disclosure, the term "proximal" is used to describe the side of a component, e.g., a shaft, a handle assembly, etc., closer to a user operating the surgical instrument, e.g., a surgeon, and the term "distal" is used to describe the side of the component farther from the user operating the surgical instrument.

Aspects of the present disclosure are presented for a single electrosurgical device configured for grasping tissue and performing sealing procedures using electrical and/or other energy. An end effector of the electrosurgical device may include multiple members arranged in various configurations to collectively perform the aforementioned functions. As used herein, an end effector may be referred to as a jaw assembly or clamp jaw assembly comprising an upper jaw member and a lower jaw member where at least one of the upper jaw member and the lower jaw member may be movable relative to the other. Jaw members may be adapted to connect to an electrosurgical energy source. A jaw member may incorporate an electrode. The electrode may be a positive or negative electrode. In a bipolar electrosurgical device, the electrodes may be adapted for connection to the opposite terminals of the electrosurgical energy source, such as a bipolar radio frequency (RF) generator, so as to generate a current flow therebetween. An electrosurgical energy may be selectively communicated through tissue held between the jaw members to effect a tissue seal and/or treatment. Tissue may be coagulated from the current flowing between the opposite polarity electrodes on a jaw member.

At least one jaw member may include a knife channel defined therein configured to reciprocate a knife therealong for severing tissue held between the jaw members. The knife channel may be an extended slot in the jaw member. The knife may be provided within a recess associated with the at least one jaw member. The electrosurgical device may have both coagulation and cutting functions. This may eliminate or reduce instrument interchange during a surgery. Cutting may be achieved using mechanical force alone or a combination of mechanical force and the electrosurgical energy. The electrosurgical energy may be selectively used for coagulation and/or cutting. The knife may be made from an electrically conductive material adapted to connect to the electrosurgical source, and selectively activatable to separate tissue disposed between the jaw members. The knife may be spring biased such that once tissue is severed, the knife may automatically return to an unengaged position within the knife channel or a retracted position in the recess.

In some aspects, the jaw members may be movable relative to each other. During operation of the electrosurgical device, at least one of the jaw members may move from a first, open position where the jaw members can be disposed around a mass of tissue, to a second, closed position where the jaw members grasp the tissue. The jaw members therefore may move through a graspers-like range of motion, similar to that of conventional pliers. In the second position, current flows between the jaw members to achieve hemostasis of the tissue captured therebetween. The jaw members may be configured to have a relatively thick proximal portion to resist bending. At least one of the jaw members may have a three-dimensional configuration with a D-shaped cross-sectional. The three-dimensional configuration with the D-shaped cross-sectional may resist bending. A lock mechanism may be included to lock the jaw members in the closed position. The lock mechanism may set the clamp pressure between the jaw members. At least one electrically conductive gap setting member may be provided between the jaw members to establish a desired gap between electrodes in bipolar electrosurgical devices.

The electrosurgical device may incorporate components to set a gap between the jaws of the end effector, grasp a tissue via the end effector, deliver energy to the tissue via one or more electrodes, and cut the tissue via a dissecting device such as a tissue knife. The structural capabilities of any aspect of an electrosurgical device may be designed for use in one or more of a variety of surgical procedures. In some surgical procedures, the treated tissue may be readily accessible to an end effector affixed to a relatively straight and unbendable shaft. In some alternative surgical procedures, the tissue may not be readily accessible to the end effector on such a shaft. In such procedures, the electrosurgical device may incorporate a shaft designed to bend so that the end effector may contact the tissue requiring treatment. In such a device, the shaft may include one or more articulated joints that may permit the shaft to bend under control by the user. A sliding knife may include a feature to provide actuating force to the sliding knife. A knife actuator may be operably coupled to the shaft for selectively reciprocating the knife through the knife channel.

A front portion assembly may be designed for a specific surgical procedure, while a reusable handle assembly, configured to releasably attach to a front portion assembly, may be designed to provide control of surgical functions common to each front portion assembly, such as tissue grasping, cauterizing, and cutting. Consequently, the number and types of devices required for surgeries can be reduced. The reusable handle assembly may be designed to automate common functions of the electrosurgical device. Device intelligence may be provided by a controller located in the reusable handle assembly that is configured to receive information from a front portion assembly. Such information may include data regarding the type and use of the front portion assembly. Alternatively, information may include data indicative of the position and/or activation of control components (such as buttons or slides that can be manipulated) that may indicate what system functions should be activated and in what manner.

In some non-limiting examples, the controller may supply the RF current when the energy activation control is placed in an activating position by the user. In some alternative non-limiting examples, the controller may supply the RF current for a predetermined period of time once the energy activation control is placed in an activating position. In yet another non-limiting example, the controller may receive data related to the position of the jaw members and prevent the RF current from being supplied to the to the one or more tissue power contacts if the jaw members are not in a closed position.

In some aspects, any of the mentioned examples also may be configured to articulate along at least one axis through various means, including, for example, a series of joints, one or more hinges or flexure bearings, and one or more cam or pulley systems. Other features may include cameras or lights coupled to one or more of the members of the end effector, and various energy options for the surgical device.

The electrosurgical device can be configured to source energy in various forms including, without limitation, electrical energy, monopolar and/or bipolar RF energy, microwave energy, reversible and/or irreversible electroporation energy, and/or ultrasonic energy, heat energy, or any combination thereof, to the tissue of a patient either independently or simultaneously. The energy can be transmitted to the electrosurgical device by a power source in electrical communication with the electrosurgical device. The power source may be a generator. The power source may be connected to the electrosurgical device via a suitable transmission medium such as a cable. The power source may be separate from the electrosurgical device or may be made integrally with the electrosurgical device to form a unitary electrosurgical system. In one non-limiting example, the power source may include one or more batteries located within a portion of the electrosurgical device. It may be understood that the power source may source energy for use on the tissue of the patient as well as for any other electrical use by other devices, including, without limitation, lights, sensors, communication systems, indicators, and displays, which operate in relation to and/or with the electrosurgical device to form an electrosurgical system.

As disclosed above, the electrosurgical device may be configured to source electrical energy in the form of RF energy. The electrosurgical device can transmit the RF energy through tissue compressed between two or more jaw members. In some surgical procedures, RF energy may be useful for removing, shrinking, or sculpting soft tissue while simultaneously sealing blood vessels. RF energy may work particularly well on connective tissue, which is primarily composed of collagen and shrinks when contacted by heat. Because a sharp boundary may be created between the affected tissue and the surrounding tissue, surgeons can operate with a high level of precision and control, without sacrificing untargeted adjacent tissue.

The RF energy may be in a frequency range described in EN 60601-2-2:2009+A11:2011, Definition 201.3.218—HIGH FREQUENCY. For example, the frequency in monopolar RF applications may be typically restricted to less than 5 MHz. However, in bipolar RF applications, the frequency can be almost anything. Frequencies above 200 kHz can be typically used for monopolar applications in order to avoid the unwanted stimulation of nerves and muscles that would result from the use of low frequency current. Lower frequencies may be used for bipolar applications if the risk analysis shows the possibility of neuromuscular stimulation has been mitigated to an acceptable level. Normally, frequencies above 5 MHz are not used in order to minimize the problems associated with high frequency leakage currents. Higher frequencies may, however, be used in the case of bipolar applications.

As discussed above, the electrosurgical device may be used in conjunction with a generator. The generator may be an electrosurgical generator characterized by a fixed internal impedance and fixed operating frequency that deliver maximum power to an external load (e.g., tissue) having an electrical impedance in the range of about 1 ohm to about 500 ohms. In this type of bipolar electrosurgical generator, the applied voltage may increase monotonically as the load impedance increases toward the maximum "open circuit" voltage as the load impedance increases to levels of tens of thousands of ohms or more. In addition, the electrosurgical device may be used with a bipolar electrosurgical generator having a fixed operating frequency and any one or more of a substantially constant output voltage, output current, or output power over a range of load impedances of tens of ohms to tens of thousands of ohms including "open circuit" conditions. The electrosurgical device may be advantageously used with a bipolar electrosurgical generator of either a variable voltage design or substantially constant voltage design in which the applied voltage may be interrupted when the delivered current decreases below a predetermined level. Such bipolar generators may be referred to as automatic generators in that they may sense the completion of the coagulation process and terminate the application of voltage, often accompanied by an audible indication in the form of a cessation of a "voltage application" tone or the annunciation of a unique "coagulation complete" tone. Further, the electrosurgical device may be used with an electrosurgical generator whose operating frequency may vary with the load impedance as a means to modulate the applied voltage with changes in load impedance.

Various aspects of electrosurgical devices use therapeutic and/or sub-therapeutic electrical energy to treat tissue. Some aspects may be utilized in robotic applications. Some aspects may be adapted for use in a hand operated manner. In one non-limiting example, an electrosurgical device may include a proximal handle, a distal working end or end effector, and an introducer or elongated shaft disposed in-between.

In some non-limiting medical procedures, the electrosurgical device may be used to weld or seal vessels prior to tissue resection. Such vessels also may be removed as part of procedures to resect other tissue such as cysts, tumors, or infected materials. Blood vessel sealing may reduce bleeding, thereby decreasing potential harmful effects during a resection procedure. In such procedures, vessels may be cut at the seal location. It may be understood that complete sealing may be required at the site of the cut to prevent bleeding. It is therefore useful to have an electrosurgical device that may be prevented from cutting a vessel until complete sealing is assured.

To properly seal vessels, two mechanical parameters that affect thickness of the sealed vessel may be accurately controlled: the pressure applied to the vessel and the gap between the electrodes. Proper sealing may require that sufficient pressure is placed on the vessel to assure that the vessel walls are proximate to each other and no intervening gap remains therebetween. The vessel may be compressed to a pressure within a predetermined range. A typical range of appropriate pressures may be between about 30 pounds per square inch (about 0.2 MPa) and about 250 pounds per square inch (about 1.7 MPa). In some alternative aspects, a range of appropriate pressures may be between about 250 pounds per square inch (about 1.7 MPa) and about 1050 pounds per square inch (about 7.2 MPa). In addition, proper sealing may require that sufficient power is provided to assure that the vessel walls receive sufficient heat to weld the walls together. Thus, both tissue compression and sufficient electrosurgery device power may be required to form a proper seal. These can be achieved by the jaw members of the end effector. As mentioned above, the jaw members may grasp, compress, and deliver the energy to the tissue.

To effectively carry out hemostasis, the jaw members should efficiently conduct a proper current flow through the grasped tissue. When that current is insufficient, coagulation of the tissue or vessel may be compromised. When the current is excessive, correspondingly excessive heating may occur with a potential for the generation of damaging electrical arcing. Excessive heating may result in the phenomenon of tissue and blood coagulum sticking to the surface of the jaw members. This may result in increased electrical impedance between the electrodes of the device and the tissue that may subsequently be grasped for the purpose of treatment. Such sticking tissue may evoke a disruption of the coagulated surface, which in itself may compromise the intended hemostatic effect. The end effector may incorporate highly polished electrode surfaces for the purpose of reducing the extent of tissue sticking as well as to facilitate their cleaning when sticking does occur.

When grasping tissue, the jaw members may come into mutual contact, causing a short circuit. For example, when a small tissue component is grasped between the jaw members and/or when the jaw members are compressed hard, the electrodes may be in contact with each other in the vicinity of the grasped tissue, causing short-circuiting. The jaw members may include insulative coatings that may be in contact in some geometry.

In various aspects, an electrically conductive gap setting member may be provided between the jaw members. The electrically conductive gap setting member may be affixed on and/or integral to one jaw member and extend to the other jaw member. The electrically conductive gap setting member may protrude through the jaw member. The electrically conductive gap setting member may define a gap between the jaw members. The electrically conductive gap setting member may be electrically conductive. The gap setting member may be made of a material that is electrically conductive and also is stiff to resist deformation in response to an applied force. The electrically conductive gap setting member may be sized and configured to avoid short-circuiting between the opposing electrodes and/or ensure that the electrodes would not close enough to arc without the presence of tissue between the electrodes.

In various aspects, the electrodes on the surfaces of the jaw members may be made of metal. The exposed portions of the surfaces of the jaw members may have smooth surfaces to minimize sticking to tissue or coagulum and to facilitate their cleaning when tissue debris or coagulum does accumulate. The surfaces of the jaw members may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members may include laminar composites of thermally conductive copper and a mechanically stronger material, particularly, higher modulus stainless steel. Biocompatibility of the jaw members may be maintained through an electro-deposited biocompatible metal coating, such as chromium, that coats both the stainless steel and copper laminate while not affecting the electrically insulative members. In some non-limiting examples, for end effectors with small jaw members, for example, having a width of about 0.039" (1 mm) at their tip, laminar composites having a layer of 304 stainless steel of thickness of about 0.011" and a corresponding layer of copper having about 0.052" thickness may be provided. For larger jaw members, laminar composites having a layer of 304 stainless steel of thickness about 0.015" and a corresponding layer of copper having about 0.075" to about 0.085" thickness may be provided. The biocompatible coating may be provided, for example, as an electro-deposited chromium coating, for example, that identified as MED-COAT 2000 marketed by Electrolyzing Corporation of Ohio, Cleveland, Ohio 44112. This biocompatible coating is described as meeting or exceeding USP Class VI certification.

In various aspects, the length of the jaw members may be set for the particular application in surgery. For example, the length of the jaw members of about 0.4" or 0.5" to about 0.75", such as about 0.47" (12 mm), may be used for smaller anatomical structures or fine work. For larger anatomical structures, the length of the jaw members may be about 1" or greater, for example, about 1.57" (40 mm).

As disclosed above, the exposed portions of the surfaces of the jaw members may have smooth surfaces to minimize sticking to tissue or coagulum and to facilitate their cleaning when tissue debris or coagulum does accumulate. The surfaces of the jaw members may include thermally conductive components such as copper, silver, aluminum, tungsten, nickel, or any other thermally conductive materials that may occur to those skilled in the art. Laminar composites coated with a biocompatible metal coating may be applied to the surfaces. The jaw members may include laminar composites of thermally conductive copper and a mechanically stronger material, particularly, higher modulus stainless steel. It may be recognized that tissue or coagulum may nevertheless adhere to the jaw members even for jaw members having smooth surfaces. As a result, it may be difficult to remove the sealed tissue from the jaw members to permit the end effector to be moved from one location to another. Manual removal of such tissue or coagulum from the jaw members may adversely affect the quality of the seal of the tissue produced by the electrosurgical device.

In some aspects, non-stick metal coatings may comprise coatings that may be used to reduce or prevent the ability of other materials to stick to metal surface, for example fried eggs to a non-stick material coated pan. Properties of such non-stick coatings may include a low surface energy value. A surface energy value may be used to quantify the disruption of intermolecular bonds that occur when a surface is created. The surface energy may therefore be considered as the excess energy at the surface of a material compared to the bulk, or the work required to build an area of a particular surface. Another way to view the surface energy is to relate it to the work required to cut a bulk sample, thereby creating two surfaces. Table 1 presents some exemplary values of surface energy for a number of materials.

TABLE 1

Surface Energy of Sample Materials

| Material | Surface Energy (mJ/m$^2$) |
| --- | --- |
| Copper | 1103 |
| Aluminum | 840 |
| Zinc | 753 |
| Stainless Steel | 700-1100 |
| Aluminum oxide - sapphire | 638 |
| Tin | 526 |
| Lead | 458 |
| Silicon dioxide - silica | 287 |
| Glass/Porcelain | 250-500 |
| Mica | 120 |
| Polyimides | 46 |
| Polyvinylchloride | 42 |
| Aliphatic or Semi-aromatic Polyamides | 41 |
| Polystyrene | 40 |
| Polyethylene | 32 |
| Polytetrafluoroethylene | 18 |
| Polyhexafluoropropylene | 12 |

For purposes of comparison, stainless steel may typically have a surface energy value of about 700 mJ/m$^2$ (dyne/cm) to about 1000 mJ/m$^2$ (dyne/cm) which promotes low adhesion (low adhesion results in lower sticking). Non-stick materials, however, may have surface energy values of about 50 mJ/m$^2$ to about 40 mJ/m$^2$. Non-limiting examples of such surface energy values for non-stick materials may include values of about 50 mJ/m$^2$, about 48 mJ/m$^2$, about 46 mJ/m$^2$, about 44 mJ/m$^2$, about 42 mJ/m$^2$, about 40 mJ/m$^2$, and any value or range of values therebetween including endpoints. Such non-stick materials may include common polymers, such as aliphatic or semi-aromatic polyamides (for example Nylon) and polyimides (for example, Kapton®). It may be recognized that the surface energy values of such polymers are much lower than that of, for example, stainless steel, and thus may be less prone to sticking. Other materials, having even lower surface energy values—for example, in the range of about 40 mJ/m$^2$ to about 12 mJ/m$^2$—may be even more resistant to sticking. Non-limiting examples of such surface energy values for non-stick materials may include values of about 40 mJ/m$^2$, about 36 mJ/m$^2$, about 32 mJ/m$^2$, about 28 mJ/m$^2$, about 24 mJ/m$^2$, about 20 mJ/m$^2$, about 16 mJ/m$^2$, about 12 mJ/m$^2$, and any value or range of values therebetween including endpoints. Polytetrafluoroethylene (PTFE) is one such material, having a surface energy of about 18 mJ/m$^2$. Still other materials may have even lower values of surface free energy, such as those materials having surface micro- and/or nano-structures that may take advantage of the "lotus leaf effect." The surface free energy of such materials, natural or man-made, may have a value of about 5 mJ/m$^2$. In some non-limiting aspects, therefore, a non-stick material may be one having a non-zero, positive-valued surface energy less than that of stainless steel. For example, a non-stick material may have a surface energy of less than about 1100 mJ/m$^2$ to about 5 mJ/m$^2$. Thus, in some general non-limiting examples, such surface energy values of a non-stick material may include values of about 1100 mJ/m$^2$, about 1000 mJ/m$^2$, about 900 mJ/m$^2$, about 800 mJ/m$^2$, about 700 mJ/m$^2$, about 600 mJ/m$^2$, about 500 mJ/m$^2$, about 400 mJ/m$^2$, about 300 mJ/m$^2$, about 200 mJ/m$^2$, about 100 mJ/m$^2$, about 50 mJ/m$^2$, about 40 mJ/m$^2$, about 30 mJ/m$^2$, about 20 mJ/m$^2$, about 10 mJ/m$^2$, about 5 mJ/m$^2$, and any value or range of values therebetween including endpoints.

Such non-stick coatings may be electrically conductive or non-conductive. Electrically conductive non-stick coatings may be sufficiently conducting to permit electrical current to pass into the tissue contacted by jaws of an electrosurgical device to effect localized heating and tissue sealing. However, portions of jaw members coated with an electrically non-conductive coating will not permit electrical current to pass into the tissue. It may be suspected that an amount of adhesive (sticking) force of a tissue to a jaw member having a non-stick surface coating may decrease as the amount of surface area coated increases. However, it may also be suspected that the amount of tissue sealing, which may be related to the quality of the seal, could be significantly reduced for a jaw member completely or almost completely coated with the electrically non-conductive non-stick material.

However, the effect of such non-stick surface coatings on the quality of electrosurgery-based vessel seals has not been well determined. Disclosed below are results of controlled tests of the effect of the amount of electrically non-conducting non-stick coatings on the quality of electrosurgery-based vessel seals. Such tests measure both the adhesive force of tissue to the jaw members as well as the effectiveness of electrosurgery-based vessel seals produced within the tissues. Such tests have revealed the unexpected result that jaw members having even a high percentage (greater than 70%) of surface coating with a non-conductive non-stick material may produce electrosurgery-based vessel seals that are functionally equivalent to those formed by uncoated jaw members. Additional tests, not previously seen, further reveal the effectiveness of different coating geometries on both the adhesive force and the quality of electrosurgery-based vessel seal. The results of such tests demonstrate the additional unexpected result that the efficacy of tissue electrosurgery-based vessel seals may further depend on the geometry of the coating on the jaw member and not simply on the amount of the surface coated with the non-stick material.

For the purpose of this disclosure, the term "patterned coating" is defined as a material coating on a surface, in which the pattern is defined by one or more geometric components, and the patterned coating is specifically fabricated to include the one or more geometric components. In this definition, the term specifically fabricated is taken to mean that the pattern is intentionally designed and that a fabrication method of the patterned coating is repeatable or potentially repeatable over any number of surfaces. It may be further understood that the patterned coating may include a material coating comprising one or more portions removed from the material, the patterned coating may include a pattern of portions of the coating material applied to the surface, or the patterned coating may be fabricated by an overmolding process.

In the following detailed description, reference is made to the accompanying drawings, which form a part hereof. In the drawings, similar symbols and reference characters typically identify similar components throughout the several views, unless context dictates otherwise.

Figure 1B:
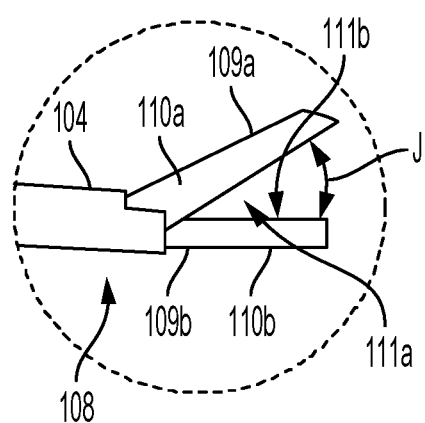
FIG. 1B is a detailed view of the end effector of the surgical instrument shown in FIG. 1A, according to one aspect of the present disclosure.

FIG. 1A shows an electrosurgical instrument 100 in electrical communication with a generator 101, according to one aspect of the present disclosure. The electrosurgical instrument 100 may be configurable with a flexible circuit 102 according to various aspects. The electrosurgical instrument 100 may comprise an elongate member 103, such as a shaft 104, having a proximal portion 105 coupled to a handle assembly 106. A distal portion 107 of the elongate member 103 may comprise an end effector 108 (see FIG. 1B) coupled to a distal end of the shaft 104. In some aspects, the end effector 108 may comprise a first jaw member 109a and a second jaw member 109b, each having an outer portion or surface 110a, 110b. At least one of the first jaw member 109a and the second jaw member 109b may move relative to the shaft 104. There may be only one jaw movable relative to the shaft 104, and the other jaw may be fixed relative to the shaft 104. At least one of the first jaw member 109a and the second jaw member 109b may be rotatably movable relative to the other along a path shown by arrow J to transition the first and second jaw members 109a, 109b between open and closed positions. In operation, the first and second jaw members 109a, 109b may be transitioned from the open position to a closed position to capture tissue therebetween. Captured tissue may contact one or more working portions of the jaw set 111a, 111b configured to apply energy to treat target tissue located at or near the end effector 108.

The type of energy may take various forms and includes, without limitation, monopolar and/or bipolar RF energy, microwave energy, reversible and/or irreversible electroporation energy, and/or ultrasonic energy, or any combination thereof. The handle assembly 106 may comprise a housing 112 defining a grip 113. In various aspects, the handle includes one or more control interfaces 114a-c, e.g., a button or switch 114a, rotation knob 114b rotatable along arrow R, and a trigger 114c movable relative to the grip 113 along arrow T, configured to provide operation instructions to the end effector 108. Multiple buttons, knobs, or triggers described also may be included as part of the housing 112 in order to manipulate one or more of the functioning members at the end effector 108. In some aspects, the handle assembly 106 may be further configured to electrically couple to a generator 101 to supply the electrosurgical instrument 100 with energy.

The generator 101 may be connected to the electrosurgical instrument 100 via a suitable transmission medium such as a cable 115. In one example, the generator 101 may be coupled to a controller, such as a control unit 116, for example. In various aspects, the control unit 116 may be made integrally with the generator 101, or may be provided as a separate circuit module or device electrically coupled to the generator 101 (shown in phantom to illustrate this option). The control unit 116 may include automated or manually operated controls to control the amount of current delivered by the generator 101 to the electrosurgical instrument 100. Although, as presently disclosed, the generator 101 is shown separate from the electrosurgical instrument 100, in some aspects, the generator 101 (and/or the control unit 116) may be made integrally with the electrosurgical instrument 100 to form a unitary electrosurgical system where a battery located within the electrosurgical instrument 100 may be the energy source and a circuit coupled to the battery produces the suitable electrical energy, ultrasonic energy, or heat energy. While the generator 101 is illustrated as generally coupled to the handle assembly 106, e.g., with a cord, it is to be understood that in some aspects the generator 101 may be positioned within the elongate member 103 and/or the handle assembly 106. For example, in one aspect, the generator 101 comprises one or more direct current batteries positioned in the handle assembly 106, shaft 104, or a portion thereof.

In one aspect, the generator 101 may comprise an input device located on a front panel of the generator 101. The input device may comprise any suitable device that generates signals suitable for programming the operation of the generator 101, such as a keyboard, or input port, for example. In one example, one or more electrodes in the first jaw 109a and one or more electrodes in the second jaw member 109b may be coupled to the generator 101. The cable 115 may comprise multiple electrical conductors for the application of electrical energy to a first electrode (which may be designated as a + electrode) and to a second electrode (which may be designated as a −electrode) of the electrosurgical instrument 100. It may be recognized that + and −designations are made solely for convenience and do not indicate an electrical polarity. An end of each of the conductors may be placed in electrical communication with a terminal of the generator 101. The generator 101 may have multiple terminals, each configured to contact one or more of the conductors. The control unit 116 may be used to activate the generator 101, which may serve as an electrical source. In various aspects, the generator 101 may comprise an RF source, an ultrasonic source, a direct current source, and/or any other suitable type of electrical energy source, for example, one which may be activated independently or simultaneously. In various aspects, the cable 115 may comprise at least one supply conductor 117 and at least one return conductor 118, wherein current can be supplied to the electrosurgical instrument 100 via the at least one supply conductor 117 and wherein the current can flow back to the generator 101 via the at least one return conductor 118. In various aspects, the at least one supply conductor 117 and the at least one return conductor 118 may comprise insulated wires and/or any other suitable type of conductor. As described below, the at least one supply conductor 117 and the at least one return conductor 118 may be contained within and/or may comprise the cable 115 extending between, or at least partially between, the generator 101 and the end effector 108 of the electrosurgical instrument 100. The generator 101 can be configured to apply a sufficient voltage differential between the supply conductor 117 and the return conductor 118 such that sufficient current can be supplied to the end effector 108 to perform the intended electrosurgical operation.

In one example, the generator 101 may be implemented as an electrosurgery unit (ESU) capable of supplying power sufficient to perform bipolar electrosurgery using RF energy. In one example, the ESU can be a Force Triad™ Energy Platform sold by Medtronic of Boulder Colo. In some aspects, such as for bipolar electrosurgery applications, an electrosurgical instrument 100 having an active electrode and a return electrode can be utilized, wherein the active electrode and the return electrode can be positioned against, adjacent to, and/or in electrical communication with the tissue to be treated such that current can flow from the active electrode, through the tissue, and to the return electrode. Thus, in various aspects, the electrosurgical system may comprise a supply path and a return path, wherein the captured tissue being treated completes, or closes, the circuit. In other aspects, the generator 101 may provide sub-therapeutic RF energy levels for purposes of evaluating tissue conditions and providing feedback in the electrosurgical system. Such feedback may be employed to control the therapeutic RF energy output of the electrosurgical instrument 100. Sub-therapeutic RF energy levels may be used for bipolar surgical procedures if a risk analysis shows the possibility of neuromuscular stimulation has been mitigated to an acceptable level. Under some conditions, frequencies above 5 MHz may not be used in order to minimize problems associated with high frequency leakage currents. However, higher frequencies may be used in the case of bipolar techniques.

During operation of electrosurgical instrument 100, the user generally grasps tissue, supplies energy to the grasped tissue to form a weld or a seal (e.g., by an actuating button and/or pedal), and then drives a tissue-cutting member at the distal end of the electrosurgical instrument through the grasped tissue. According to various aspects, a jaw-closing member may be provided, and the translation of the axial movement of the jaw-closing member may be paced, or otherwise controlled, to aid in driving the jaw-closing member at a suitable rate of travel. By controlling the rate of travel, the likelihood that the captured tissue has been properly and functionally sealed prior to transection with the cutting member may be increased.

Figure 2:
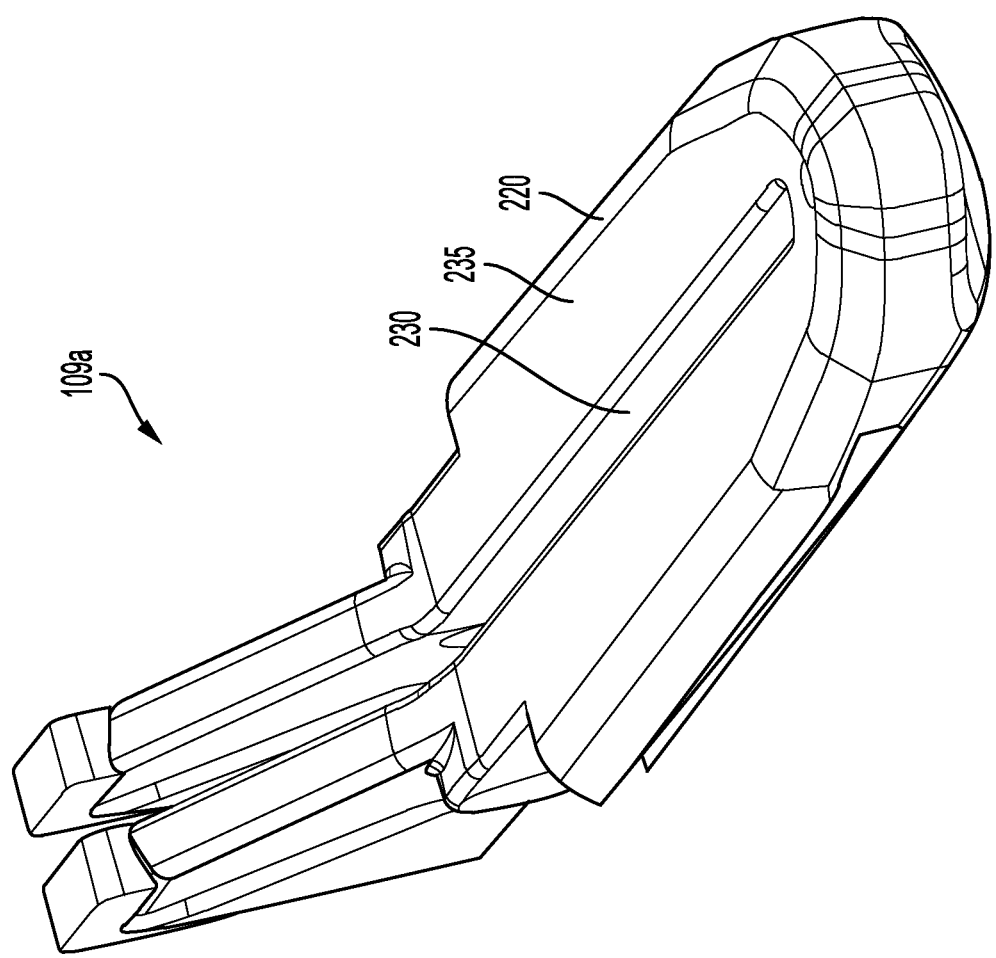
FIG. 2 illustrates a perspective view of one aspect of a first jaw of the end effector of the electrosurgical instrument depicted in FIGS. 1A and 1B.

FIG. 2 is a perspective view of one example of a first jaw member 109a of a surgical instrument system 100. The first jaw member 109a may include at least a first electrode 220. The electrode 220 may comprise an electrically conducting material. In various aspects, the electrode 220 of the jaw member 109a, may be made of metal. The surface of the jaw member 109a may include thermally conductive components such as stainless steel, copper, silver, aluminum, tungsten, nickel, or any other thermally conductive materials that may occur to those skilled in the art. Laminar composites coated with a biocompatible metal coating may be applied to the surfaces. The jaw member 109a may include laminar composites of thermally conductive copper and a mechanically stronger material, particularly, higher modulus stainless steel. Biocompatibility of the jaw member 109a may be maintained through an electro-deposited biocompatible metal coating, such as chromium, that coats both the stainless steel and copper laminate. In one example, the electrode 220 may have a U-shape that surrounds a knife channel 230, in which a knife may be disposed to reciprocate.

As depicted in FIG. 2, a non-stick coating 235 may be deposited on or otherwise placed in direct physical communication with the electrode surface. In some non-limiting examples, the non-stick coating 235 may comprise an electrically conductive coating. In other non-limiting examples, the non-stick coating 235 may comprise an electrically non-conductive coating. While not explicitly depicted in FIG. 2, the non-stick coating 235 may be deposited directly on the entire surface of the electrode 220 or may be deposited directly on one or more portions of the surface of the electrode 220. Multiple portions of the non-stick coating 235 may be contiguous or non-contiguous. In some alternative aspects, portions of the non-stick coating 235 deposited on the surface of the electrode 220 may be removed thereby exposing portions of the surface of the electrode 220. Alternatively, features comprising one or more depressions may be fabricated in the surface of the electrode 220 and the non-stick coating 235 may be deposited only within the depressions. It may be understood that the non-stick coating 235 may be deposited or otherwise placed in direct physical communication with the electrode surface according to any suitable fabrication method. Non-limiting examples of such fabrication methods may include patterned printing or the use of an overmolding process.

Although FIG. 2 depicts a first jaw member 109a, it may be understood that a second jaw member 109b may be similarly coated with a non-stick coating. The second jaw member 109b may be coated with the same non-stick coating as the first jaw member 109a, or with a different non-stick coating. The non-stick coating on the second jaw member 109b may be deposited directly on the entire surface of an electrode associated with the second jaw member 109b or may be deposited directly on one or more portions of the surface of the electrode associated with the second jaw member 109b. Multiple portions of the non-stick coating on the surface of the electrode associated with the second jaw member 109b may be contiguous or non-contiguous. In some alternative aspects, portions of the non-stick coating on the electrode associated with the second jaw member 109b may be removed thereby exposing portions of the surface of the electrode associated with the second jaw member 109b. Alternatively, features comprising one or more depressions may be fabricated in the surface of the electrode associated with the second jaw member 109b and the non-stick coating thereon may be deposited only within the depressions. Further, the disposition of the non-stick coating on the surface of the first electrode 220 may be the same as or different from the non-stick coating on the surface of the electrode associated with the second jaw member 109b.

FIGS. 3-7 and FIGS. 10-12 depict a variety of aspects of one or more jaw members comprising electrically non-conducting non-stick coatings.

Figure 3:
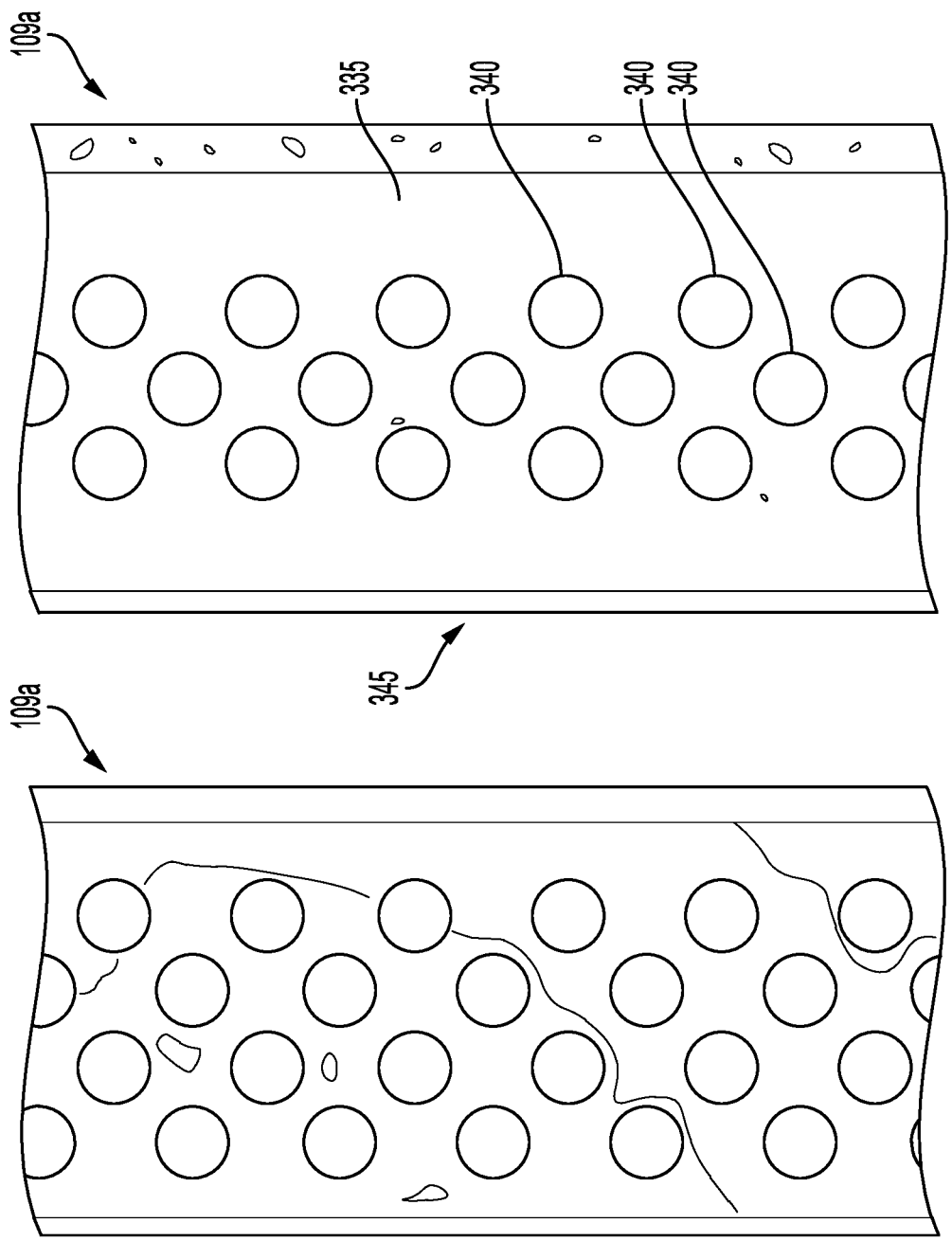
FIG. 3 depicts a first aspect of a surface of a first jaw of the end effector of the electrosurgical instrument depicted in FIGS. 1A and 1B.

FIG. 3 depicts a first jaw member 109a having an electrically conductive electrode surface that is generally coated with an electrically non-conducting non-stick coating 335. The non-stick coating 335 comprises a patterned coating 345 created by the removal of circular portions 340 of the non-stick coating. In one non-limiting example, such circular portions 340 may be removed by machining the non-stick coating 335 by a tool such as, in one non-limiting example, by an end-mill. The removal of the circular portions 340 may result in the exposure of portions of the underlying electrode surface. It may be noted that the patterned non-stick coating 345 comprises a number of linear arrays of the circular portions 340, in which the position of the circular portions 340 in the center linear array are offset from the circular portions 340 in the linear arrays on either side.

It should be recognized that the patterned coating 345 depicted in FIG. 3 is merely one non-limiting example of a patterned coating. Thus, a patterned coating may comprise a single portion or may have multiple portions removed from the coating 335. The multiple portions may be physically isolated from each other or may be contiguous. The one or more portions removed from the non-stick coating 335 may include portions that are linear, circular, elliptical, oval, rectangular, square, rounded rectangular, or have a geometry defined by any closed two-dimensional shape. A patterned coating may include a plurality of portions 340 having the same shape or may include portions having different shapes. A patterned coating may include a plurality of portions having the same size or may include portions having different sizes. The portions may be disposed in a patterned coating in any number of ways including, without limitation, regular or irregularly spaced arrays.

The patterned non-stick coating 345 depicted in FIG. 3 may be fabricated by removing portions of the of the non-stick material, for example by first contacting the non-stick material with a surface of the electrode and then using a fabrication method to remove the portions of the material to form the patterned coating. Alternative methods of fabricating the patterned non-stick coating 345 may include, for example, printing the patterned coating directly on the surface of the electrode. Additional alternative methods for producing the patterned coating 345 on the electrode may also be employed.

Figure 4:
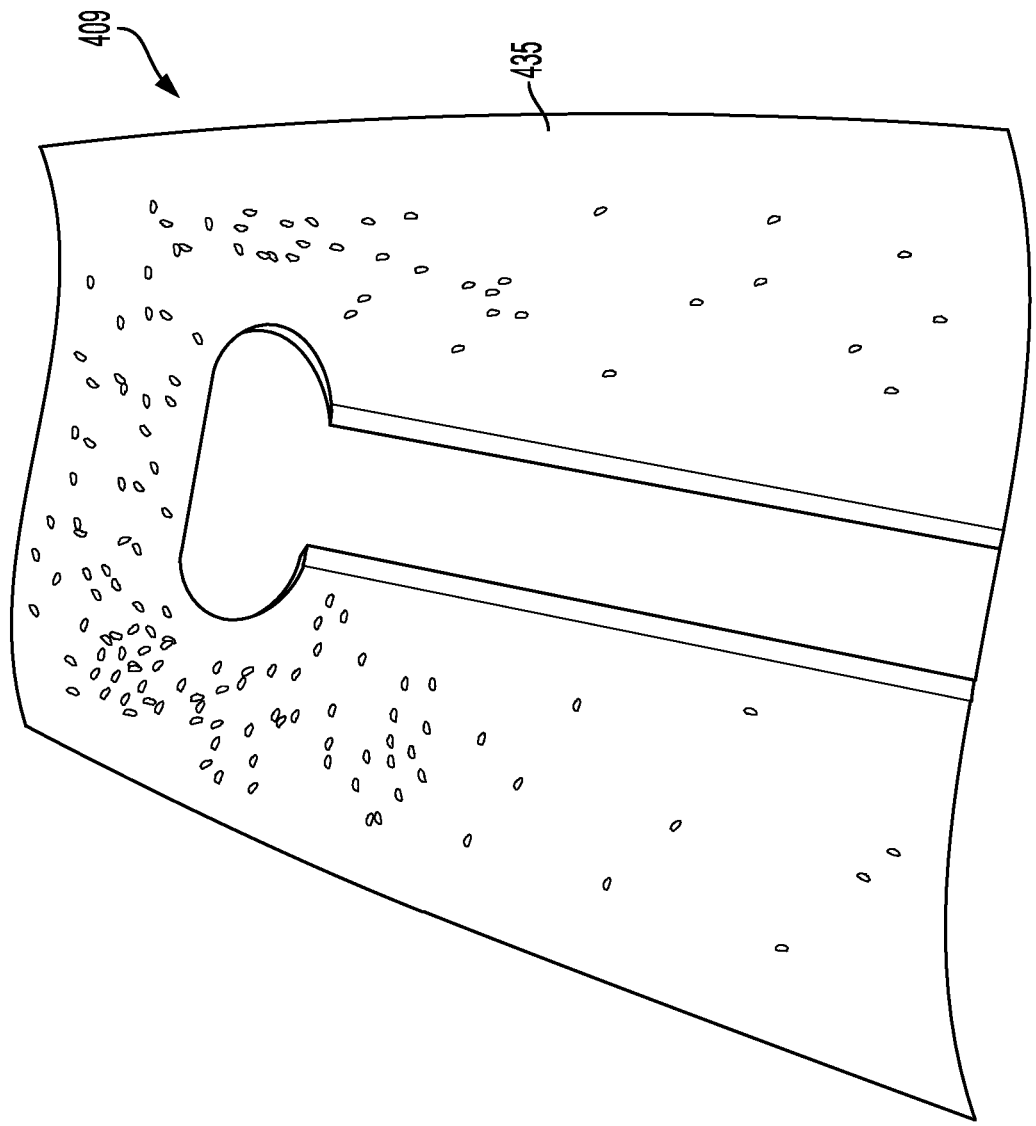
FIG. 4 depicts a second aspect of a surface of a first jaw of the end effector of the electrosurgical instrument depicted in FIGS. 1A and 1B.

FIG. 4 depicts a first jaw member 409 having an electrically non-conducting non-stick coating 435 applied to a surface of an electrode. As distinguished from the non-stick coating 335 depicted in FIG. 3, the non-stick coating 435 depicted in FIG. 4 is not a patterned coating. Thus, the non-stick coating 435 depicted in FIG. 4 comprises a plurality of coating defects (observable as discolorations and pin-holes) in the surface of the non-stick coating 435 which may be understood as unintended and non-repeatable features of the coating.

Figure 5:
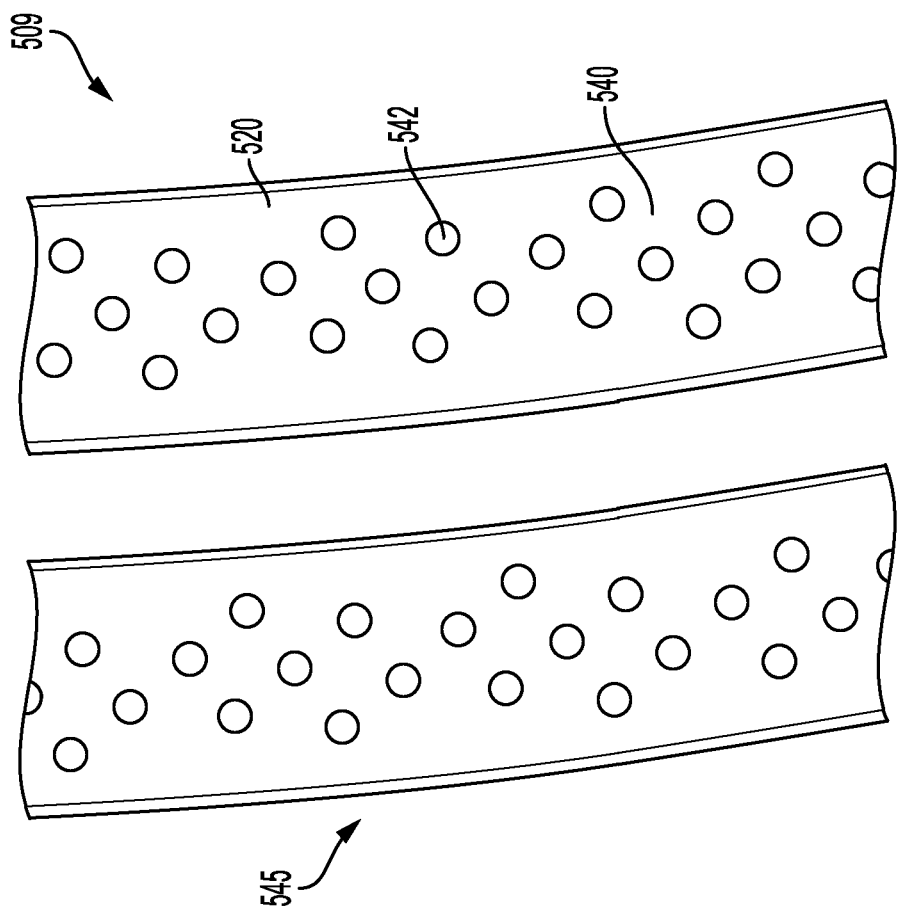
FIG. 5 depicts a third aspect of a surface of a first jaw of the end effector of the electrosurgical instrument depicted in FIGS. 1A and 1B.

FIG. 5 depicts a jaw member 509 having an electrically conductive electrode surface 520. The electrode surface 520 includes a plurality of recessed features 542. In FIG. 5, the recessed features 542 comprise a plurality of circular recessed features 542. The non-stick coating 540 may be applied to or in the plurality of recessed features 542. The patterned non-stick coating 545 may comprise the plurality of non-stick coatings 540 applied to or in the plurality of recessed features 542. It may be noted that the patterned non-stick coating 545 comprises a number of linear arrays of the circular recessed features 542 having the non-stick coating 540 applied to or in the recessed features 542, in which the linear arrays are oblique to a longitudinal axis of the jaw member 509. The non-stick coating 540 may completely fill the recessed features 542, thereby forming a surface co-planar with the electrically conductive electrode surface 520. In an alternative aspect, the non-stick coating 540 may incompletely fill the recessed features 542, thereby forming a surface recessed from the electrically conductive electrode surface 520. In yet an additional aspect, the non-stick coating 540 may overfill the recessed features 542, thereby forming a surface protruding above the electrically conductive electrode surface 520.

It should be recognized that the patterned coating 545 depicted in FIG. 5 is merely one non-limiting example of a patterned coating. Thus, a patterned coating may comprise a non-stick coating applied to or in a single recessed feature or multiple recessed features. The recessed features may be physically isolated from each other or may be contiguous. The one or more recessed features may extend partially through a thickness of the electrode. Alternatively, the one or more recessed features may extend completely through the thickness of the electrode, thereby allowing the recessed feature to receive the non-stick coating either from a top side or a bottom side of the electrode, for example as part of an overmolding process. The one or more recessed features may include recessed features that are linear, circular, elliptical, oval, rectangular, square, rounded rectangular, or have a geometry defined by any closed two-dimensional shape. A patterned coating may include the non-stick coating disposed within a plurality of recessed features having the same shape or may include recessed features having different shapes. A patterned coating may include the non-stick coating disposed within a plurality of recessed features having the same size or may include recessed features having different sizes. The pattern coating may include the non-stick coating disposed within recessed features that may be disposed in a surface of an electrode in any number of ways including, without limitation, regular or irregularly spaced arrays.

The patterned non-stick coating 545 depicted in FIG. 5 may be fabricated by removing portions from the surface of the electrode to form the recessed features, for example by the use of an end-mill, and then using a fabrication method to deposit the non-stick material in the recessed features to form the patterned coating. Alternative methods of fabricating the patterned non-stick coating 545 may include, for example, molding the electrode to include the recessed features before depositing the non-stick materials therewithin. Additional alternative methods for producing the patterned coating 545 on the electrode may also be employed.

Figure 6:
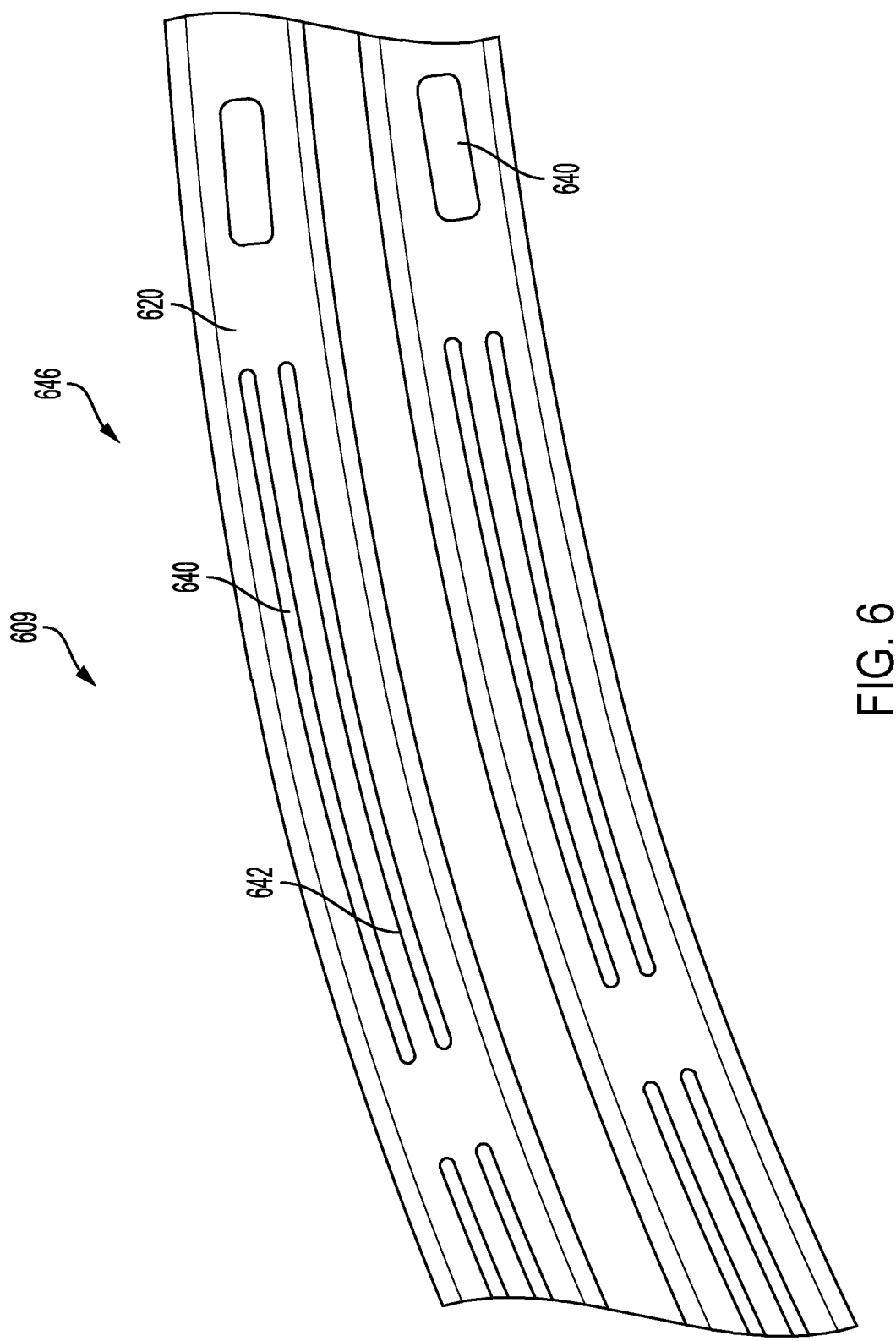
FIG. 6 depicts a fourth aspect of a surface of a first jaw of the end effector of the electrosurgical instrument depicted in FIGS. 1A and 1B.

FIG. 6 depicts a jaw member 609 having an electrically conductive electrode surface 620. The electrode surface 620 includes a plurality of recessed features 642. In FIG. 6, the recessed features 642 comprise a plurality of elongated recessed features 642. The non-stick coating 640 may be applied to or in the plurality of recessed features 642. The patterned non-stick coating 645 may comprise the plurality of non-stick coating 640 applied to or in the plurality of recessed features 642. It may be noted that the patterned non-stick coating 645 comprises the non-stick coating 640 applied to or in the plurality of elongated recessed features 642 that are arrayed along or parallel to the longitudinal axis of the jaw member 609. The non-stick coating 640 may completely fill the recessed features 642, thereby forming a surface co-planar with the electrically conductive electrode surface 620. In an alternative aspect, the non-stick coating 640 may incompletely fill the recessed features 642, thereby forming a surface recessed from the electrically conductive electrode surface 620. In yet an additional aspect, the non-stick coating 640 may overfill the recessed features 642, thereby forming a surface protruding above the electrically conductive electrode surface 620.

It should be recognized that the patterned coating 645 depicted in FIG. 6 is merely one non-limiting example of a patterned coating. Thus, a patterned coating may comprise a single elongated recessed feature or may have multiple elongated recessed features. The elongated recessed features may be physically isolated from each other or may be contiguous. The one or more recessed features may extend partially through a thickness of the electrode. Alternatively, the one or more recessed features may extend completely through the thickness of the electrode, thereby allowing the recessed feature to receive the non-stick coating either from a top side or a bottom side of the electrode, for example as part of an overmolding process. More complex patterned coatings may be derived from combinations of elongated recessed features to form, a non-limiting examples, a herring-bone pattern or a T-shaped pattern, A patterned coating may include the non-stick coating disposed within a plurality of elongated recessed features having the same shape or may include elongated recessed features having different shapes. For example, the elongated features may have the same length or may have different lengths. Additionally, the elongated features may have the same width or may have different widths. The pattern coating may include the non-stick coating disposed within elongated recessed features that may be disposed in a surface of an electrode in any number of ways including, without limitation, regular or irregularly spaced arrays.

The patterned non-stick coating 645 depicted in FIG. 6 may be fabricated by removing portions from the surface of the electrode to form the elongated recessed features, for example by the use of an end-mill, and then using a fabrication method to deposit the non-stick material in the elongated recessed features to form the patterned coating. Alternative methods of fabricating the patterned non-stick coating 645 may include, for example, molding the electrode to include the elongated recessed features before depositing the non-stick materials therewithin. Additional alternative methods for producing the patterned coating 645 on the electrode may also be employed.

Figure 7:
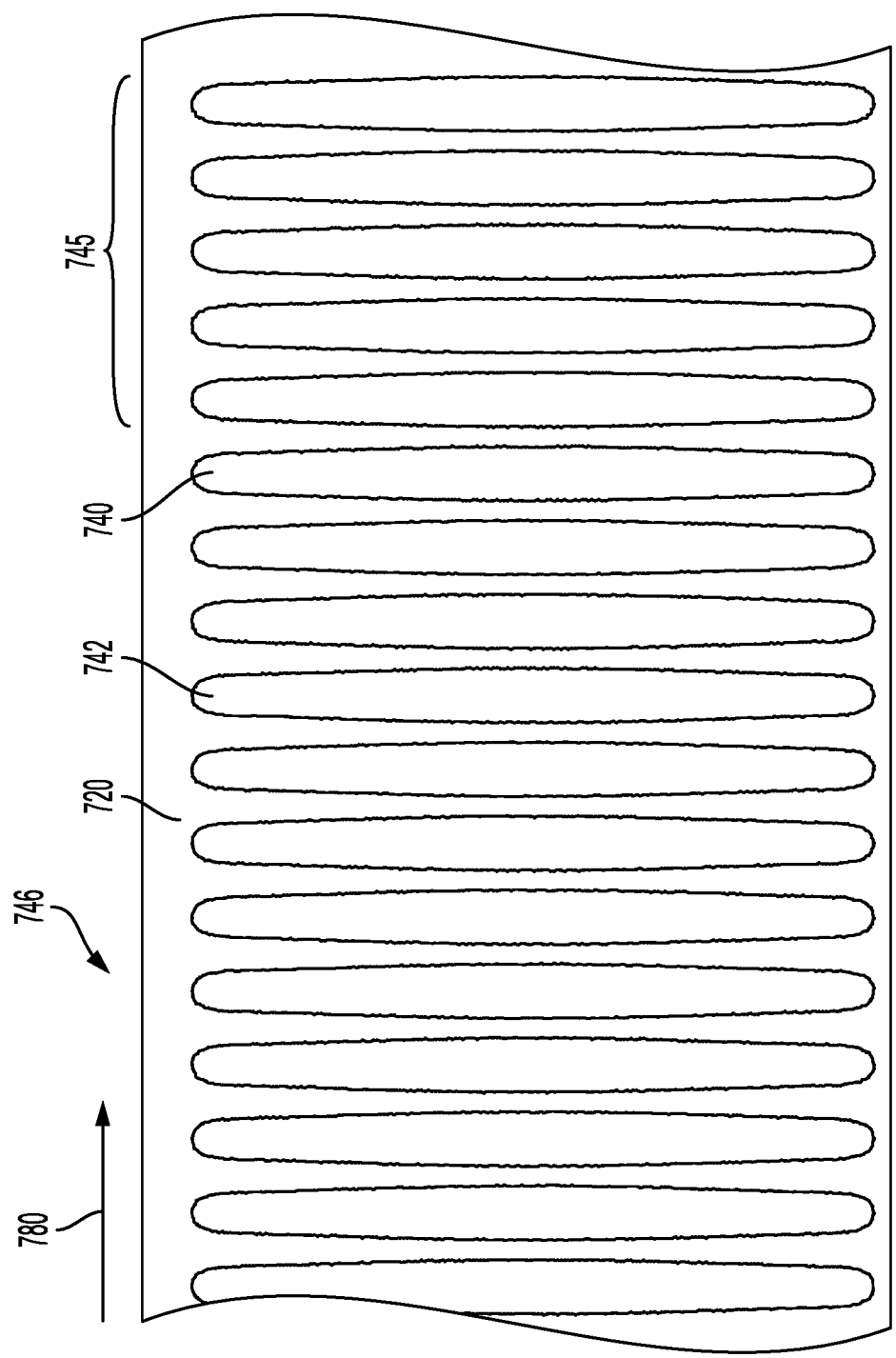
FIG. 7 depicts a fifth aspect of a surface of a first jaw of the end effector of the electrosurgical instrument depicted in FIGS. 1A and 1B.

FIG. 7 depicts a close-up view of a jaw member having an electrically conductive electrode surface 720. The electrode surface 720 includes a plurality of recessed features 742. In FIG. 7, the recessed features 742 comprise a plurality of elongated recessed features 742. The non-stick coating 740 may be applied to or in the plurality of recessed features 742. The patterned non-stick coating 745 may comprise the plurality of non-stick coating 740 applied to or in the plurality of recessed features 742. It may be noted that the patterned non-stick coating 745 comprises the non-stick coating 740 applied to or in the plurality of elongated recessed features 742 that are arrayed along or parallel to a transverse axis 780 of the jaw member. The non-stick coating 740 may completely fill the recessed features 742, thereby forming a surface co-planar with the electrically conductive electrode surface 720. In an alternative aspect, the non-stick coating 740 may incompletely fill the recessed features 742, thereby forming a surface recessed from the electrically conductive electrode surface 720. In yet an additional aspect, the non-stick coating 740 may overfill the recessed features 742, thereby forming a surface protruding above the electrically conductive electrode surface 720.

It should be recognized that the patterned coating 745 depicted in FIG. 7 is merely one non-limiting example of a patterned coating. Thus, a patterned coating may comprise a single elongated recessed feature or may have multiple elongated recessed features. The elongated recessed features may be physically isolated from each other or may be contiguous. The one or more recessed features may extend partially through a thickness of the electrode. Alternatively, the one or more recessed features may extend completely through the thickness of the electrode, thereby allowing the recessed feature to receive the non-stick coating either from a top side or a bottom side of the electrode, for example as part of an overmolding process. More complex patterned coatings may be derived from combinations of elongated recessed features to form, a non-limiting examples, a herring-bone pattern or a T-shaped pattern, A patterned coating may include the non-stick coating disposed within a plurality of elongated recessed features having the same shape or may include elongated recessed features having different shapes. For example, the elongated features may have the same length or may have different lengths. Additionally, the elongated features may have the same width or may have different widths. The pattern coating may include the non-stick coating disposed within elongated recessed features that may be disposed in a surface of an electrode in any number of ways including, without limitation, regular or irregularly spaced arrays.

The patterned non-stick coating 745 depicted in FIG. 7 may be fabricated by removing portions from the surface of the electrode to form the elongated recessed features, for example by the use of an end-mill, and then using a fabrication method to deposit the non-stick material in the elongated recessed features to form the patterned coating. Alternative methods of fabricating the patterned non-stick coating 745 may include, for example, molding the electrode to include the elongated recessed features before depositing the non-stick materials therewithin. Additional alternative methods for producing the patterned coating 745 on the electrode may also be employed.

Figure 8:
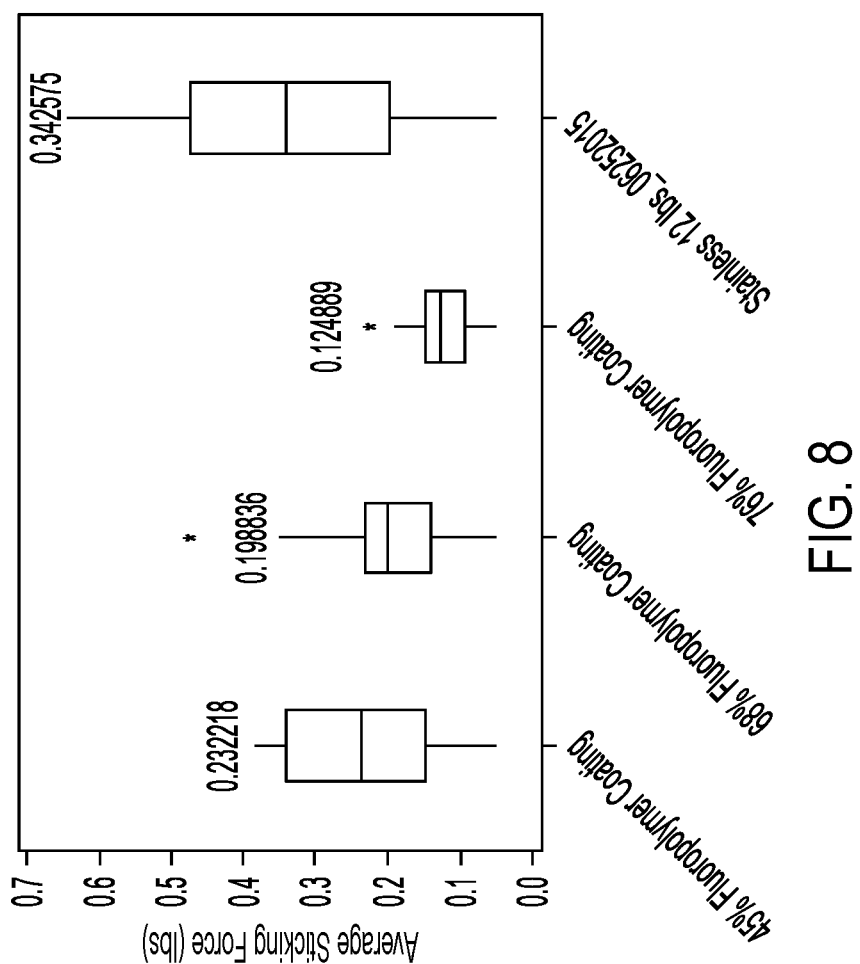
FIG. 8 depicts a boxplot of the sticking force of a tissue to a first jaw of an end effector of the electrosurgical instrument depicted in FIGS. 1A and 1B, wherein the surface of the first jaw may comprise one of a number of percent coatings of a non-stick material.

FIG. 8 depicts a box plot of measurements of average total sticking force (lbf) for tissues sealed using an electrosurgical device having a jaw member that includes an electrode comprising a variety of patterned non-stick coating. The total adhesion force is the integral of the tissue sticking force over the surface area where sticking occurs. By reducing the area of sticking, the total sticking force can be reduced. In FIG. 8, the patterned non-stick coating is similar to that depicted in FIG. 7 and the non-stick material may be a fluoropolymer. The test tissue materials used in FIG. 8 are samples of carotid artery material. FIG. 8 compares the total sticking force of the tissues sealed by jaw members in which the electrode has a surface comprising a defined amount of surface area covered by the non-stick material. A control result, using an uncoated electrode, is included for comparison. The amount of surface area of the electrode covered by the non-stick material is presented as a percent of the total surface area of the electrode that is covered by the non-stick material. Thus, the percent total surface area of the electrode covered by the non-stick material may be calculated as $$\frac{A_m}{A_t} \times 100,$$

where $A_t$ is the total surface area of the electrode, and $A_m$ is the amount of the total surface area of the electrode covered by the non-stick material.

The box plot in FIG. 8 shows the average sticking force in lbf for carotid tissues sealed by an electrode having a 45%, 68%, and 76% surface coating of the fluoropolymer. As indicated in FIG. 8, the average total sticking force of the material to the electrodes having the three values of percent total surface area covered by the non-stick material are about 0.232 lbf, 0.199 lbf, and 0.125 lbf, respectively. These values may be compared to the value of 0.342 lbf for the control, uncoated, electrode. The boxplot suggests that the average sticking force for tissue to the electrodes decreases as the percent total surface area covered by the fluoropolymer increases. It is especially noted that the average sticking force for tissue to an electrode having 76% of its surface coated with the fluoropolymer appears to be significantly less than the control, uncoated electrode.

Figure 9:
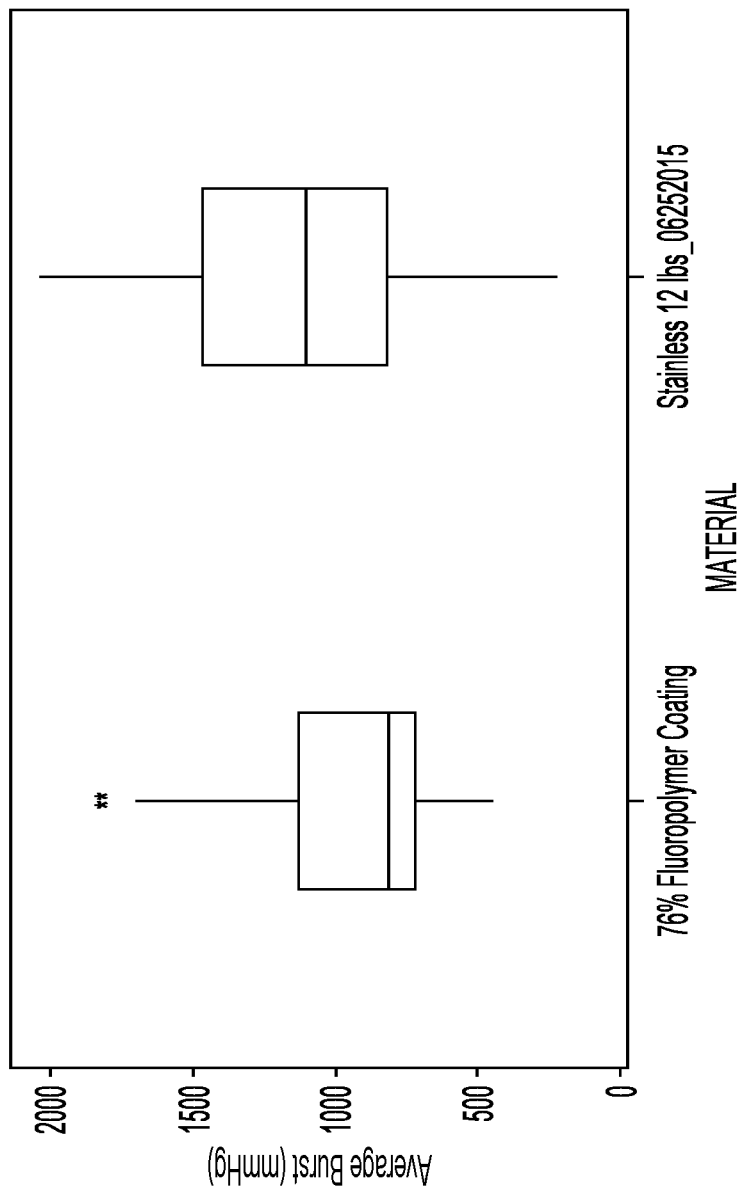
FIG. 9 depicts a boxplot of a tissue burst pressure of a tissue sealed by the end effector of the electrosurgical instrument depicted in FIGS. 1A and 1B, wherein the surface of the first jaw may comprise one of a number of percent coatings of a non-stick material.

FIG. 9 depicts a box plot of the average burst pressure (in mmHg) of carotid artery samples sealed using an electrode having a non-stick material coating pattern as illustrated in FIG. 7. FIG. 9 compares the average burst pressure for carotid artery samples sealed using an electrode have a percent total surface area covered by the non-stick coating of about 76% with the average burst pressure of carotid artery samples sealed using an uncoated electrode. The data in FIG. 9 were analyzed using the Tukey method, and no statistically significant difference was found between the two sets of samples.

Figure 16:
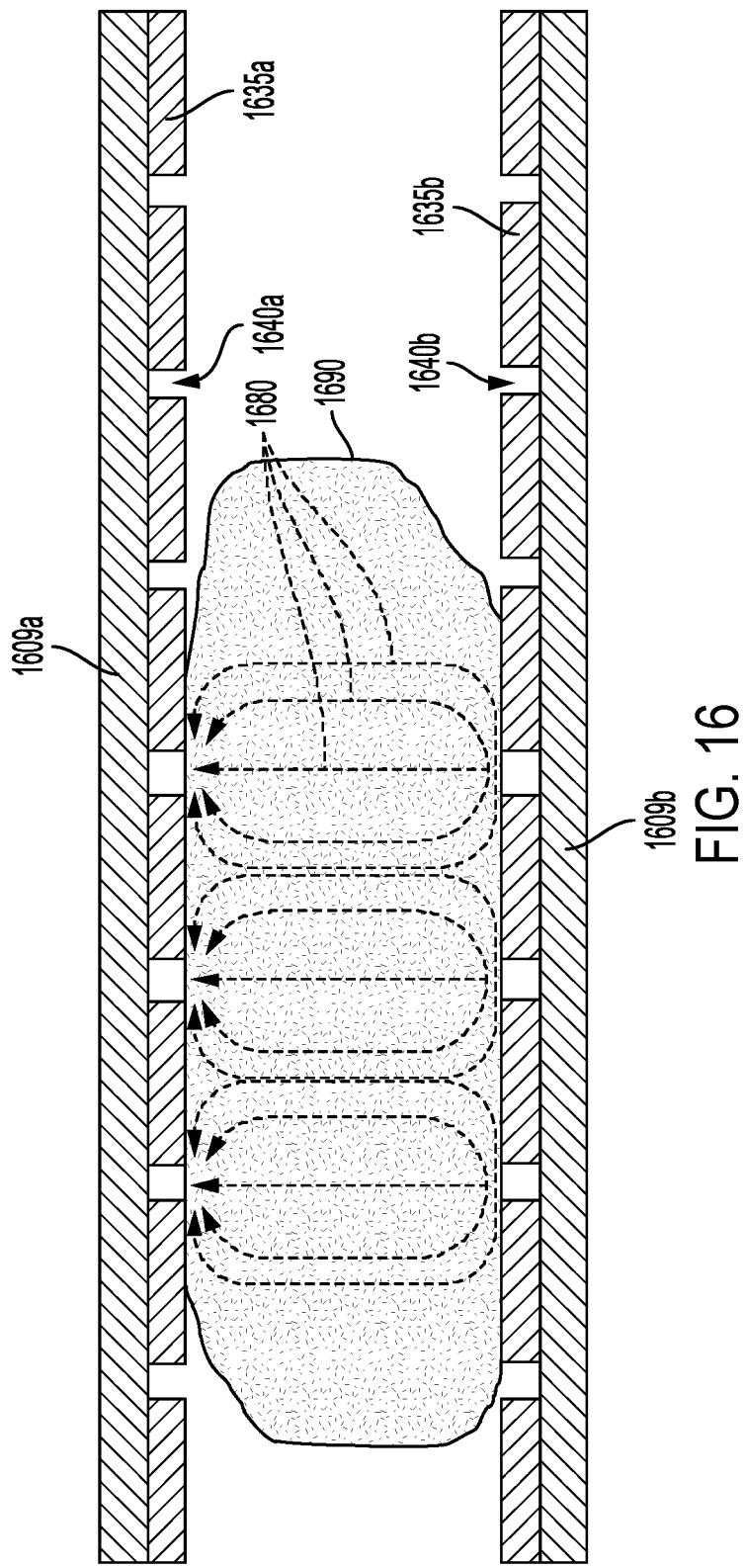
FIG. 16 depicts RF current paths through a tissue compressed between a first and a second electrode in which a surface of the first and the second electrode comprises a patterned non-stick coating.

The experimental result depicted in FIG. 9 illustrates the unexpected result that the quality of the electrosurgery-based vessel seal on a tissue is effectively unaffected even when the contact area of the conductive portion of the electrode is reduced to less than a quarter of the total surface area of the electrode. Without being bound by theory, the effect of reduced contact area on the electrical transmission of the RF energy to the tissue may be minimal because an electric current can flow laterally through the holes in the coating. FIG. 16 illustrates possible current flow pathways 1680 through a tissue 1690 compressed between a first electrode 1609*a* and a second electrode 1609*b*. Each of the first electrode 1609*a* and second electrode 1609*b* includes a patterned coating of a non-stick material, 1635*a,b*, respectively. Portions 1640*a,b* have been removed from the patterned coatings of the non-stick material 1635*a,b*, respectively, thereby exposing the electrically conductive surface of the respective electrodes 1609*a,b* underneath. It may be recognized that the portions 1640*a,b* removed from the patterned coatings of the non-stick material 1635*a,b* may provide small conductive pathways for an electrical current to flow 1680. The small conductive pathways may enable adequate electric current to flow 1680 into the tissue 1690 to raise the temperature via joule heating. As a result, the quality of the seal of a tissue sealed by an electrode having a 76% non-conductive surface coating may be about the same as the quality of the seal of a tissue sealed by an uncoated electrode.

Figure 10D:
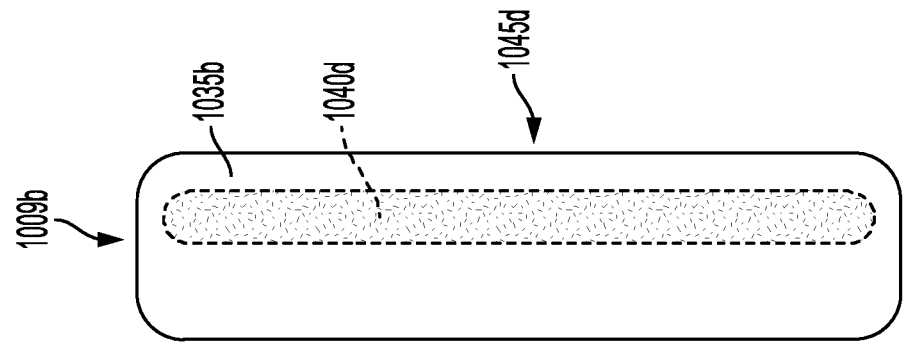
FIG. 10D depicts an aspect of a top view of a second jaw of the end effector of the electrosurgical instrument depicted in FIGS. 1A and 1B depicting surface features of the second jaw having a coating of a non-stick material FIG. 11 depict aspects of a surface of a first jaw of the end effector of the electrosurgical instrument depicted in FIGS. 1A and 1B in which the surface features are illustrated in FIG. 17A of the first jaw comprising a number of percent coatings of a non-stick material.
Figure 10C:
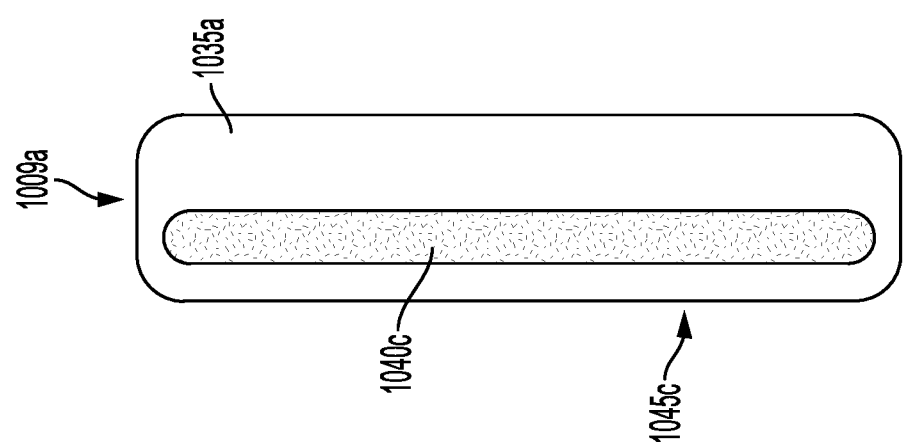
FIGS. 10A-C depict aspects of a surface of a first jaw of the end effector of the electrosurgical instrument depicted in FIGS. 1A and 1B depicting surface features of the first jaw having a coating of a non-stick material.
Figure 10B:
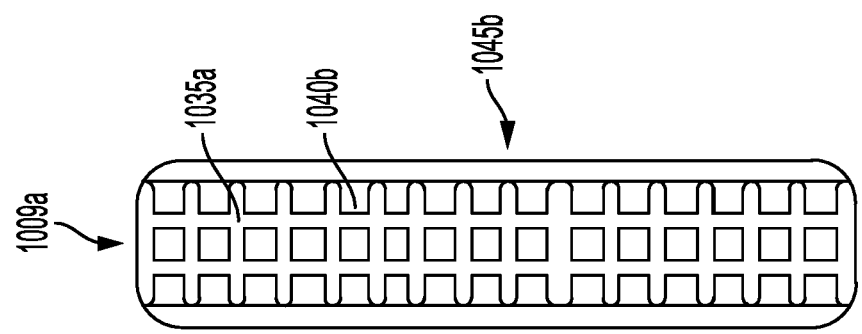
Figure 10A:
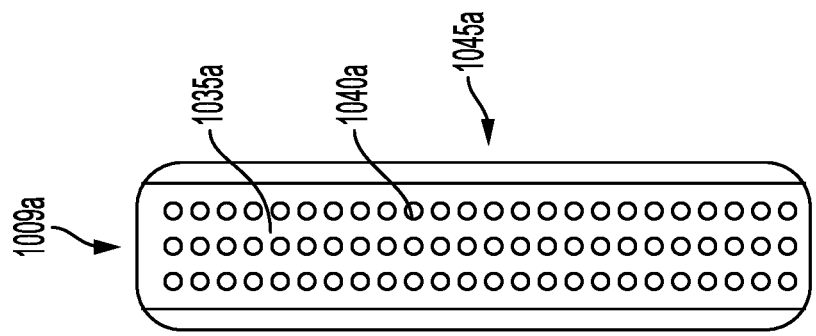

FIGS. 10A-D depict a variety of aspects of patterned coatings of non-stick material on an electrode component of an electrosurgical instrument. Thus, FIG. 10A depicts a first jaw member 1009*a* having a patterned non-stick coating 1045*a* on an electrode surface comprising a non-stick coating 1035*a* from which one or more circular portions 1040*a* have been removed, thereby uncovering the electrode surface therebelow. The patterned non-stick coating 1045*a* depicted in FIG. 10A may be fabricated by removing portions of the of the non-stick material, for example by first contacting the non-stick material with a surface of the electrode and then using a fabrication method to remove the portions of the material to form the patterned coating 1045*a*. Alternative methods of fabricating the patterned non-stick coating 1045*a* may include, for example, printing the patterned coating directly on the surface of the electrode. Additional alternative methods for producing the patterned non-stick coating 1045*a* on the electrode may also be employed.

In some aspects, the percent total surface area of the electrode covered by the patterned non-stick coating 1045*a* as depicted in FIG. 10A may be adjusted by altering the number of the one or more circular portions 1040*a* removed from the non-stick coating 1035*a*. In some alternative aspects, the percent total surface area of the electrode covered by the patterned non-stick coating 1045*a* as depicted in FIG. 10A may be adjusted by altering the size of the one or more circular portions 1040*a* removed from the non-stick coating 1035*a*. In some additional aspects, the percent total surface area of the electrode covered by the patterned non-stick coating 1045*a* as depicted in FIG. 10A may be adjusted by altering the shape of the one or more circular portions 1040*a* removed from the non-stick coating 1035*a*. It may be understood that the percent total surface area of the electrode covered by the patterned non-stick coating 1045*a* as depicted in FIG. 10A may be adjusted by altering any one or more of the number, size, or shape of the one or more circular portions 1040*a* removed from the non-stick coating 1035*a*.

FIG. 10B depicts a first jaw member 1009*a* having a patterned non-stick coating 1045*b* on an electrode surface comprising a non-stick coating 1035*b* from which one or more square or rectangular portions 1040*b* have been removed, thereby uncovering the electrode surface therebelow. The patterned non-stick coating 1045*b* depicted in FIG. 10A may be fabricated by removing portions of the of the non-stick material, for example by first contacting the non-stick material with a surface of the electrode and then using a fabrication method to remove the portions of the material to form the patterned coating 1045*b*. Alternative methods of fabricating the patterned non-stick coating 1045*b* may include, for example, printing the patterned coating directly on the surface of the electrode. Additional alternative methods for producing the patterned non-stick coating 1045*b* on the electrode may also be employed.

In some aspects, the percent total surface area of the electrode covered by the patterned non-stick coating 1045*b* as depicted in FIG. 10B may be adjusted by altering the number of the one or more square or rectangular portions 1040*b* removed from the non-stick coating 1035*b*. In some alternative aspects, the percent total surface area of the electrode covered by the patterned non-stick coating 1045*b* as depicted in FIG. 10B may be adjusted by altering the size of the one or more square or rectangular portions 1040*b* removed from the non-stick coating 1035*b*. In some additional aspects, the percent total surface area of the electrode covered by the patterned non-stick coating 1045*b* as depicted in FIG. 10B may be adjusted by altering the shape of the one or more square or rectangular portions 1040*b* removed from the non-stick coating 1035*b*. It may be understood that the percent total surface area of the electrode covered by the patterned non-stick coating 1045*b* as depicted in FIG. 10A may be adjusted by altering any one or more of the number, size, or shape of the one or more square or rectangular portions 1040*b* removed from the non-stick coating 1035*b*.

FIGS. 10C and 10D depict a surface view of a first jaw member 1009*a* and a top view of a second jaw member 1009*b*, respectively, each having a patterned non-stick coating 1045*c* and 1045*d*, respectively, on a first and second electrode surface. Each patterned non-stick coating 1045*c* and 1045*d* may comprise a non-stick coating 1035*c* and 1035*d*, respectively, from which one or more elongated portions 1040*c* and 1040*d*, respectively, have been removed, thereby uncovering the respective electrode surfaces therebelow. The patterned non-stick coatings 1045*c* and 1045*d* depicted in FIGS. 10C and 10D may be fabricated by removing portions of the of the non-stick material, for example by first contacting the non-stick material with a surface of the electrode and then using a fabrication method to remove the portions of the material to form the patterned coatings 1045*c,d*. Alternative methods of fabricating the patterned non-stick coatings 1045*c,d* may include, for example, printing the patterned coating directly on the surface of the electrode. Additional alternative methods for producing the patterned non-stick coatings 1045c,d on the electrodes may also be employed.

FIG. 10C depicts a view of the surface of jaw member 1009a, while FIG. 10D depicts a top view of the second jaw member 1009b, in which the patterned coating 1045d is seen as a projection. Depending on the size and shape of the elongated portions 1040c and 1040d, placing the first jaw member 1009a in FIG. 10C proximate to the second jaw member 1009b in FIG. 10D may result in no overlap, a partial overlap, or a complete overlap of the elongated portion 1040c with elongated portion 1040d. In an example of the patterned coating 1045c and patterned coating 1045d in which there is no overlap between elongated portion 1040c with elongated portion 1040d, it is possible that a transmission of an RF electric current between the first electrode and the second electrode may result in the current being transmitted in a transverse manner through a tissue compressed therebetween. Alternatively, if there is at least some overlap between elongated portion 1040c with elongated portion 1040d, it is possible that a transmission of an RF electric current between the first electrode and the second electrode may result in the current being transmitted in a vertical manner through a tissue compressed therebetween In some aspects, the percent total surface area of the electrode covered by the patterned non-stick coating 1045c,d as depicted in FIGS. 10C and 10D, respectively, may be adjusted by altering the number of the one or more elongated portions 1040c,d removed from the respective non-stick coatings 1035c,d. In some alternative aspects, the percent total surface area of the electrode covered by the patterned non-stick coatings 1045c,d as depicted in FIGS. 10C and 10D, respectively, may be adjusted by altering the size (length and/or width) of the one or more elongated portions 1040c,d removed from the respective non-stick coatings 1035c,d. In some additional aspects, the percent total surface area of the electrodes covered by the patterned non-stick coatings 1045c,d as depicted in FIGS. 10C and 10D, respectively, may be adjusted by altering the shape of the one or more elongated portions 1040c,d removed from the respective non-stick coatings 1035c,d. It may be understood that the percent total surface area of the electrodes covered by the patterned non-stick coating 1045c,d as depicted in FIGS. 10C and 10D, respectively, may be adjusted by altering any one or more of the number, size (length and/or width), or shape of the one or more elongated portions 1040c,d removed from the respective non-stick coatings 1035c,d.

Figure 11:
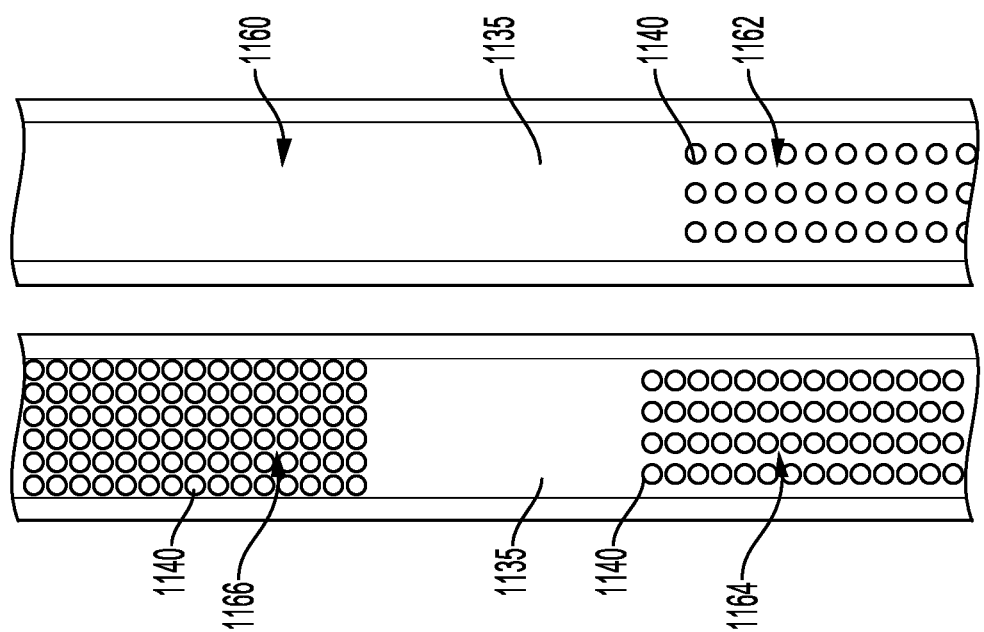

FIG. 11 illustrates a first group of patterned non-stick coatings for electrodes used to test an amount of sticking force of a tissue to the patterned coated electrode as well as burst pressure tests for seals made on the tissue (for example a carotid artery). The patterned coatings depicted in FIG. 11 were similar to those depicted in FIG. 10A. The patterned coatings were made from a non-stick coating 1135 of an electrically non-conducting material (a form of polytetrafluoroethylene) from which circular portions 1140 had been removed. The test electrodes comprised four (4) correction zones. In correction zone 1, having a first pattern 1160, no material had been removed from the non-stick coating 1135. In zone 2, having a second pattern 1162, zone 3, having a third pattern 1164, and zone 4, having a fourth pattern 1166, varying amounts of material had been removed from the non-stick coating 1135. The second, third, and fourth patterns, 1162, 1164, 1166, respectively, were fabricated by the removal of a variety of numbers of circular portions 1140. It should be noted that the circular portions 1140 removed from the non-stick coating 1135 in zones 2-4 all had the same size and shape. Thus, the percent total surface areas of the electrodes covered by the patterned non-stick coatings 1162, 1164, 1166, depended only on the relative number of circular portions 1140 removed from the non-stick coating 1135 in the respective corrective zones.

Although not illustrated, a second group of patterned non-stick coatings for electrodes were used to test an amount of sticking force of a tissue to the patterned coated electrode as well as burst pressure tests for seals made on the tissue (for example a carotid artery). The second group of patterned non-stick coatings was based on the patterned coatings depicted in FIG. 10B. Patterned coatings were made from a non-stick coating of an electrically non-conducting material (a form of polytetrafluoroethylene) from which square portions had been removed. The test electrodes having the patterned coatings depicted in FIG. 10B comprised four (4) correction zones. In correction zone 1, having a first pattern, no material had been removed from the non-stick coating. In zone 2, zone 3, and zone 4, varying amounts of material had been removed from the non-stick coating. The second, third, and fourth patterns, respectively, were fabricated by the removal of a variety of numbers of square portions. It should be noted that the square portions removed from the non-stick coating in zones 2-4 all had the same size and shape. Thus, the percent total surface areas of the electrodes covered by the patterned non-stick coatings depended only on the relative number of square portions removed from the non-stick coating in the respective corrective zones.

Figure 12:
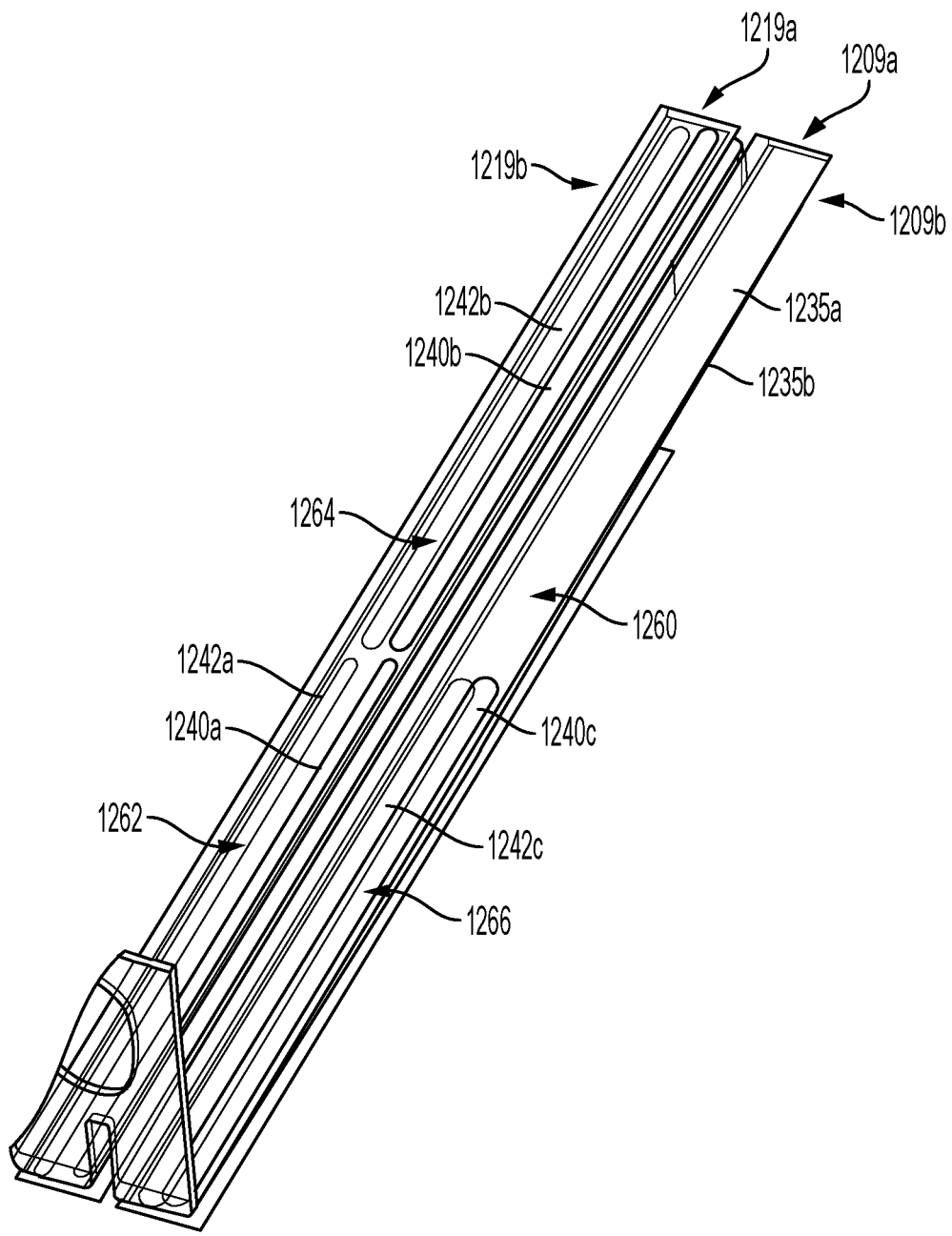
FIG. 12 depict aspects of a surface of a first jaw of the end effector of the electrosurgical instrument depicted in FIGS. 1A and 1B in which the surface features are illustrated in FIGS. 17C and 17D of the first jaw comprising a number of percent coatings of a non-stick material.

FIG. 12 illustrates a third group of patterned non-stick coatings for electrodes used to test an amount of sticking force of a tissue to the patterned coated electrode as well as burst pressure tests for seals made on the tissue (for example a carotid artery). The patterned coatings depicted in FIG. 12 were similar to those depicted in FIGS. 10C and 10D. The test electrodes comprised top test electrodes 1209a, 1219a and bottom test electrodes 1209b, 1219b. The test electrodes may be related to electrodes that form components of a first jaw member and a second jaw member, respectively, of an electrosurgical device. The patterned coatings on top electrodes 1209a, 1219a were made from a non-stick coating 1235a of an electrically non-conducting material (a form of polytetrafluoroethylene). The patterned coatings on bottom electrodes 1209b, 1219b were made from a non-stick coating 1235b of an electrically non-conducting material (a form of polytetrafluoroethylene). Although the test electrodes 1290a,b and 1219a,b were coated with the same electrically non-conducting material for the purposes of the tests disclosed herein, it may be recognized that such compositions are not limiting. Thus, patterned non-stick coating of a first electrode and a second electrode may comprise the same material or may comprise different materials. As part of the test protocol, the top test electrodes 1209a, 1219a and bottom test electrodes 1209b, 1219b were fabricated to have two different thicknesses of the non-stick coating 1235a,b. One set of test electrodes were fabricated with a non-stick coating 1235a,b having a thickness of about 0.020 inches. A second set of test electrodes were fabricated with a non-stick coating 1235a,b having a thickness of about 0.032 inches.

The patterned non-stick coatings on the top electrodes 1209a, 1219a and bottom electrodes 1209b, 1219b were formed from the respective non-stick coatings 1235a,b from which elongated portions 1240a-c and 1242a-c had been removed. The test electrodes comprised four (4) correction zones. In correction zone 1, having a first pattern 1260, no material had been removed from the non-stick coatings 1235a,b. In zone 2, having a second pattern 1262, zone 3, having a third pattern 1264, and zone 4, having a fourth pattern 1266, varying amounts of material had been removed from the non-stick coatings 1235a,b of each of the top electrodes 1209a, 1219a and bottom electrodes 1209b, 1219b thereby exposing the surface of the respective electrodes therebelow.

The elongated portions 1240a, 1242a removed from the second pattern 1262, 1240b, 1242b removed from the third pattern 1264, and 1240c, 1242c removed from the fourth pattern 1266 all had about the same length but differed in their respective widths. Thus, the percent total surface areas of the electrodes covered by the patterned non-stick coatings 1262, 1264, 1266, depended only on the relative widths of the respective elongated portions removed from the non-stick coating 1235a,b in the respective corrective zones. It may be recognized from FIG. 12 that when the top electrodes 1209a, 1219a are brought in a proximal position to the respective bottom electrodes 1209b, 1219b, portions of the respective top elongated portions may form some amount of overlap with the respective bottom elongated portions depending on the relative widths of the top elongated portions and the bottom elongated portions. For example, in zone 2, the respective widths of the elongated portions 1240a and 1242a are sufficiently narrow so that no overlap of the elongated portions occurs. Accordingly, for patterned non-stick coating 1262, an electric current passing from the top electrode 1219a to the bottom electrode 1219b would pass only in a transverse manner through any tissue compressed therebetween. In zone 3, the respective widths of the elongated portions 1240b and 1242b do not permit overlap of the elongated portions, but the edges of the respective elongated portions may be nearly aligned. Accordingly, for patterned non-stick coating 1264, an electric current passing from the top electrode 1219a to the bottom electrode 1219b may pass in an oblique manner between the edges of the respective elongated portions through any tissue compressed therebetween. In zone 4, the respective widths of the elongated portions 1240c and 1242c are sufficiently wide so that some amount of overlap of the elongated portions may occur. Accordingly, for patterned non-stick coating 1266, an electric current passing from the top electrode 1209a to the bottom electrode 1209b would pass only in a vertical manner through any tissue compressed therebetween.

Tests were conducted using electrodes having patterned non-stick coatings as disclosed above and as depicted in FIGS. 10A-D, 11, and 12 on samples of carotid arteries. The tests were designed to determine effects on both tissue sticking force and the quality of the electrosurgery-based vessel seal for tissues sealed using electrodes having different geometries and percent total surface area covered by the non-stick material. Table 2 discloses the amount of percent total surface area covered by the non-stick material for the correction zones disclosed above for each of the non-stick coating patterns. It may be understood that higher values for the correction zone number corresponded to electrodes having greater portions of the non-stick coating removed from the surface (either a greater number of circular or square portions removed from the coating, or by a larger width of the elongated portion).

TABLE 2

Percent Total Surface Area Covered by Non-stick Material

| Correction Zone Number | Circular Hole Pattern (see FIG. 11) | Square Hole Pattern (Equivalent to FIG. 11) | Elongated Pattern (See FIG. 12) |
|---|---|---|---|
| 1 | 100 | 100 | 100 |
| 2 | 80.6 | 76 | 79.9 |
| 3 | 66.5 | 60.6 | 66.6 |
| 4 | 50 | 51.5 | 56.6 |

Figure 13:
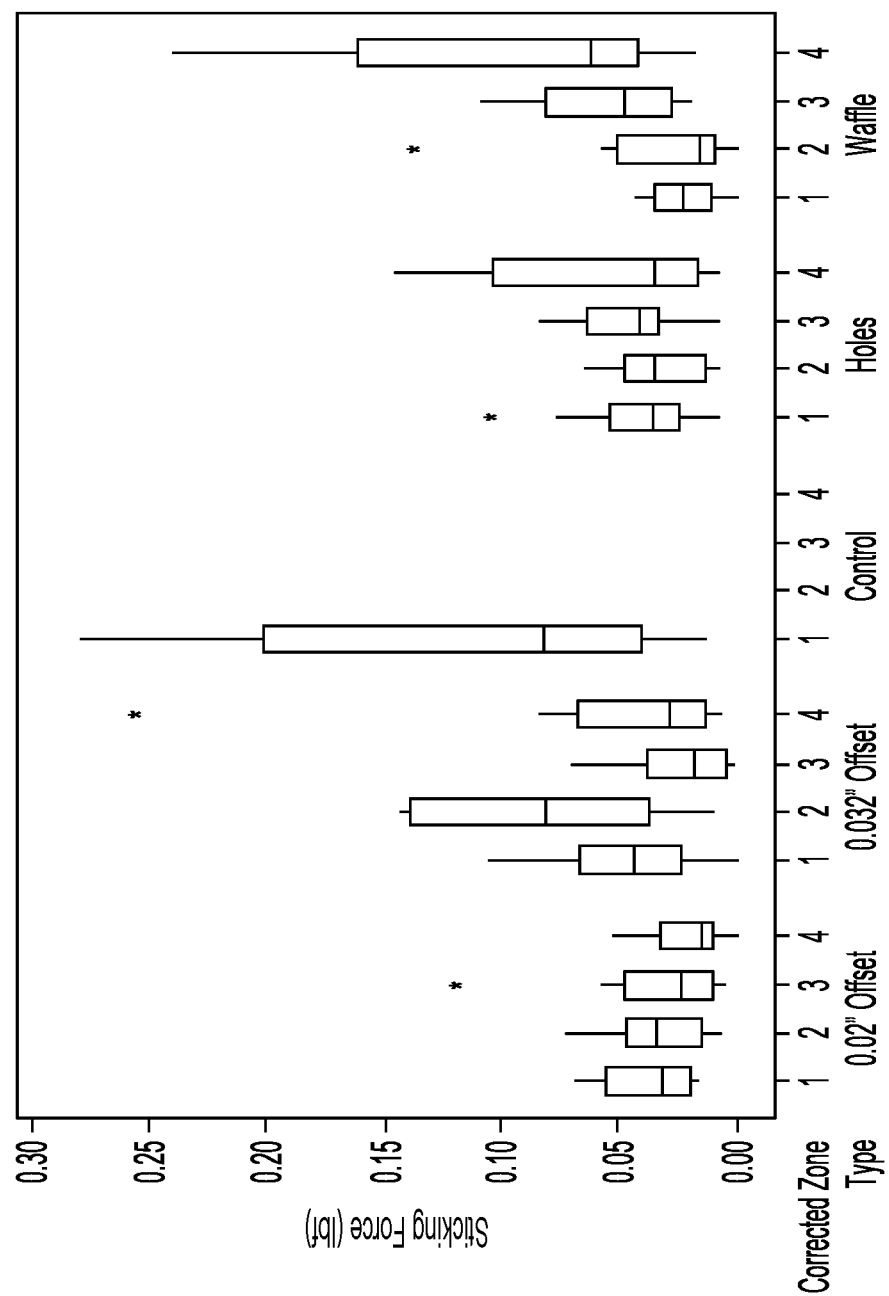
FIG. 13 depicts a boxplot of the sticking force of a tissue to a first jaw of an end effector of the electrosurgical instrument depicted in FIGS. 1A and 1B, in which the surface features are illustrated in FIGS. 17A-17D of the first jaw comprising a number of percent coatings of a non-stick material.
Figure 14:
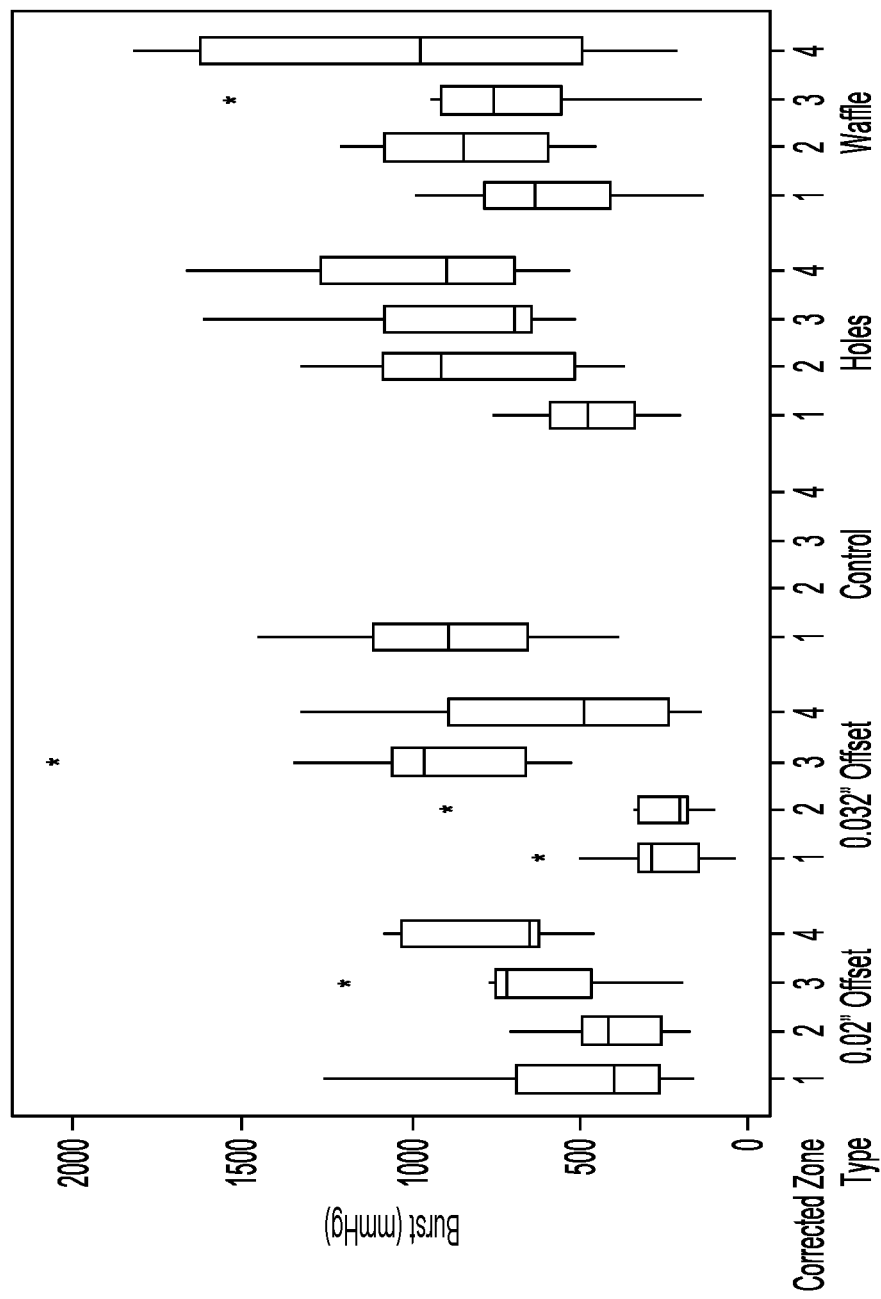
FIG. 14 depicts a boxplot of the burst pressure of a tissue sealed by the end effector of the electrosurgical instrument depicted in FIGS. 1A and 1B, in which the surface features are illustrated in FIGS. 17A-17D of the first jaw comprising a number of percent coatings of a non-stick material.
Figure 15:
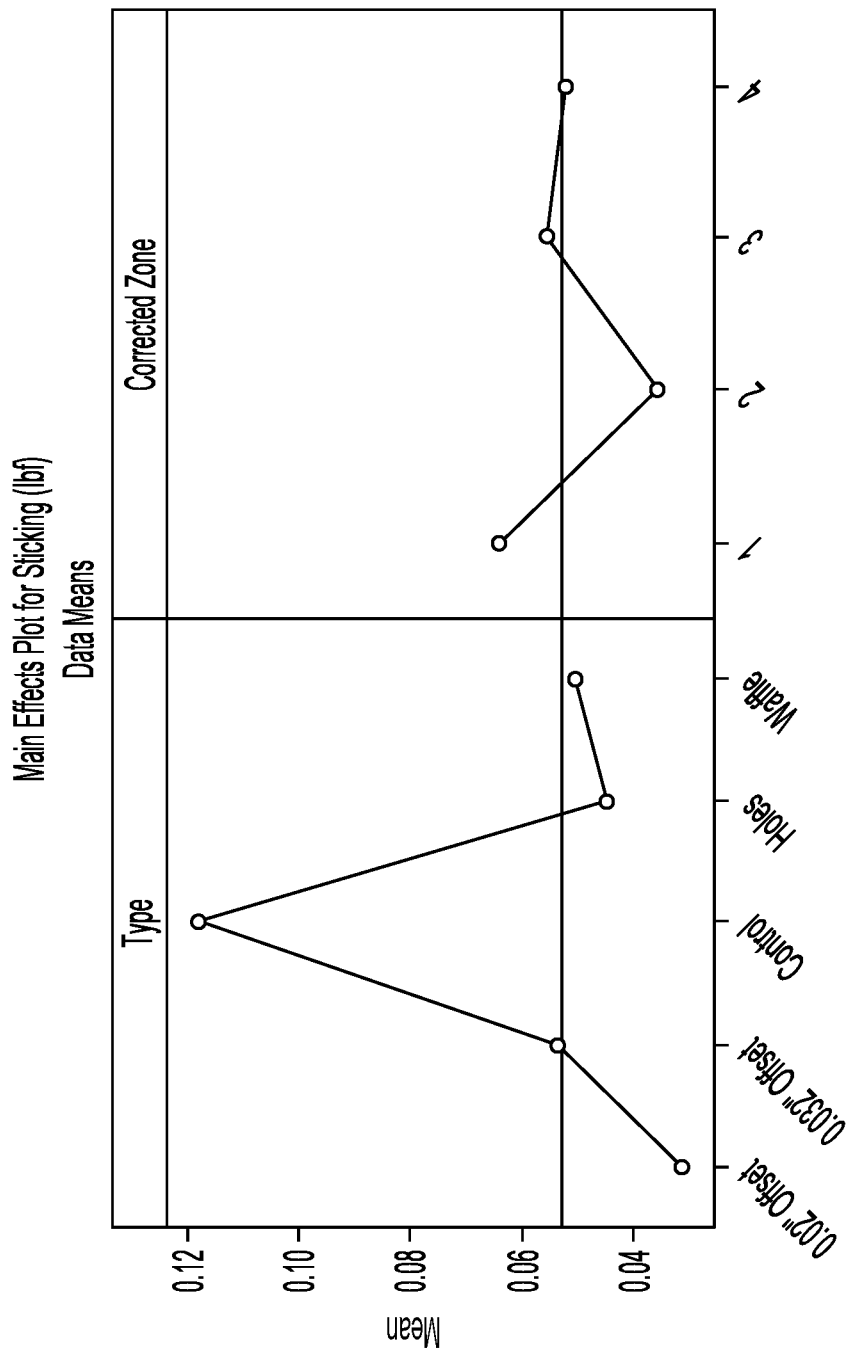
FIG. 15 depict a main effects plots, derived from the boxplots depicted in FIG. 13 of the sticking force of a tissue to a first jaw of an end effector of the electrosurgical instrument depicted in FIGS. 1A and 1B.

The graphs presented in FIGS. 13-15 reference this table by correction zone number.

FIG. 13 presents a box plot of the amount of sticking force (lbf) of sample carotid arteries to each of the sample electrodes depicted in FIGS. 10-12 and as disclosed above. The electrodes are referenced by the patterned non-stick coatings (correction zones 1-4) and types of patterned geometries. The "Correction Zone" values correspond to percent total surface area covered by the non-stick material as disclosed in Table 2, above. The "control" electrode is one having an electrically conducting silicon coating on the entire electrode surface. The "holes" pattern references the pattern depicted in FIGS. 10A and 11. The "waffle" pattern references the pattern depicted in FIG. 10B, disposed in correction zone geometries equivalent to those of the hole patterns depicted in FIG. 11. The "offset" pattern references the pattern depicts in FIGS. 10C and D and FIG. 12. Two versions of the "offset" pattern are presented, one in which the thickness of the non-stick material is about 0.02 inches thick, and the other in which the thickness of the non-stick material is about 0.032 inches thick. It may be noted that the vessels that were tested on two of the zones (Zones 2 & 4) for the 0.032" thick offset electrode were two-days old, as opposed to the one-day old vessels that were tested on the other zones. It may be observed that the sticking force for tissue sealed using the control electrode is widely distributed, while the sticking force for samples sealed using the patterned non-stick coatings were generally more narrowly distributed. Such results suggest that the patterned coatings resulted in much more repeatable sticking force of the tissues to the surface of the electrodes.

FIG. 14 presents a box plot of the burst pressure (in mmHg) of sample carotid arteries after a electrosurgery-based vessel seal had been applied by each of the sample electrodes depicted in FIGS. 10-12 and as disclosed above. The electrodes are referenced by the patterned non-stick coatings (correction zones 1-4) and types of patterned geometries. The "Correction Zone" values correspond to percent total surface area covered by the non-stick material as disclosed in Table 2, above. The "control" electrode is one having an electrically conducting silicon coating on the entire electrode surface. The "holes" pattern references the pattern depicted in FIGS. 10A and 11. The "waffle" pattern references the pattern depicted in FIG. 10B, disposed in correction zone geometries equivalent to those of the hole patterns depicted in FIG. 11. The "offset" pattern references the pattern depicts in FIGS. 10C and D and FIG. 12. Two versions of the "offset" pattern are presented, one in which the thickness of the non-stick material is about 0.02 inches thick, and the other in which the thickness of the non-stick material is about 0.032 inches thick. It may be noted that the vessels that were tested on two of the zones (Zones 2 & 4) for the 0.032" thick offset electrode were two-days old, as opposed to the one-day old vessels that were tested on the other zones.

It may be recognized that an optimal patterned non-stick material coating comprising an electrically non-conducting material may be one that minimizes the sticking force of the tissue to the electrode and maximizes the burst pressure of the seal created by the electrode. FIG. 15 depicts a main effects plot for the sticking force of the carotid artery sample to the electrodes. The main effects plot aggregates the results depicted in FIG. 13 by electrode type in the left-hand portion of the plot, and aggregates the results depicted in FIG. 13 by correction zone (that is, by percent total surface area covered by the non-stick material) in the right-hand portion of the plot. It may be observed that tissue samples sealed using electrodes having any of the non-stick material coating patterns had a lower average sticking force values to the electrodes than the control. In addition, little variation in average sticking force of the tissue to the electrodes was observed regardless of the pattern used.

FIGS. 3-7 and 19-12 and their descriptions as disclosed above present a plurality of aspects of a jaw members comprising a plurality of non-stick coating patterns. Although a plurality of aspects of such coating patterns has been disclosed herein, such aspects are not to be construed as limiting. Thus, the coating patterns may include any appropriate coating patterns that may be configured on a surface of one or more jaw members or electrodes. The coating patterns may generally include coating patterns applied to a planar surface of an electrode, to one or more raised or elevated features that extend vertically above a surface of an electrode, or to one or more depressed features that extend vertically below a surface of an electrode. It may be understood that the term "non-stick material disposed on an electrode" encompasses the application of the material on a planar surface of an electrode, to one or more raised or elevated features that extend vertically above a surface of an electrode, or to one or more depressed features that extend vertically below a surface of an electrode. No limitations, expressed or implied, are herein imposed on methods of fabricating the coating patterns.

The coating patterns may include a single feature or multiple features. The single feature or multiple features may have a limited extent, such as a small circular portion of the non-stick material disposed on an electrode (for example, FIG. 5) or a small circular portion removed from a non-stick material coating the electrode (for example, FIG. 3). The single feature or multiple features may have a more extended extent such as an elongated portion of the non-stick material disposed on an electrode (for example, FIGS. 6 and 7) or an elongated portion removed from a non-stick material coating the electrode (for example, FIGS. 10C,D). The single feature or multiple features—either of limited extent or of extended extent—are not limited in their respective shapes, sizes, or dimensions on an electrode surface. The single feature or multiple features—either of limited extent or of extended extent—are not limited in their respective dispositions about the surface of the electrode. Thus, as an example, elongated portion of the non-stick material may extend along an axis essentially parallel to a longitudinal axis of the electrode. Alternatively, an elongated portion of the non-stick material may extend along an axis essentially perpendicular to a longitudinal axis of the electrode. In yet another alternative example, an elongated portion of the non-stick material may extend along an axis neither essentially parallel to nor essentially perpendicular to a longitudinal axis of the first electrode.

The coating patterns may include multiple features that may include any combination or combinations of portions of the non-stick material disposed on an electrode surface or portions removed from a coating of a non-stick material disposed on the electrode surface. Multiple features may be combined. Further, multiple features may be symmetrically disposed about the surface of the electrode or they may be asymmetrically disposed about the surface of the electrode. Multiple features—either of limited extent or of extended extent—are not limited in their dispositions about the surface of the electrode with respect to each other.

An electrosurgical device such as that depicted in FIGS. 1A,B may comprise multiple jaws each having an electrode. A patterned non-stick coating may be applied to any one or more of the multiple electrodes. The patterned non-stick coating applied to any one of the multiple electrodes may comprise the same non-stick material as a patterned non-stick coating applied to any other of the multiple electrodes. Alternatively, the patterned non-stick coating applied to any one of the multiple electrodes may comprise a different non-stick material than that comprising a patterned non-stick coating applied to any other of the multiple electrodes. A non-stick coating pattern applied to any one of the multiple electrodes may comprise the same non-stick coating pattern applied to any other of the multiple electrodes. Alternatively, the non-stick coating patterned applied to any one of the multiple electrodes may comprise a different non-stick coating pattern than a non-stick coating pattern applied to any other of the multiple electrodes.

While various aspects herein have been illustrated by description of several aspects and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to,"

"operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered examples:

Example 1

An electrosurgical system comprising:
an RF current generator; a handle body; and
an end effector in mechanical communication with the handle body, the end effector comprising:
 a first jaw comprising a first energy delivery surface in electrical communication with a first terminal of the RF current generator; and
 a second jaw comprising a second energy delivery surface in electrical communication with a second terminal of the RF current generator,
 wherein at least a portion of the first energy delivery surface comprises a patterned coating of an electrically non-conducting non-stick material.

Example 2

The electrosurgical system of Example 1, wherein the first energy delivery surface has a first area and the at least portion of the first energy delivery surface comprising the patterned coating has a second area.

Example 3

The electrosurgical system of Example 2, wherein a ratio of the second area to the first area is less than or equal to about 0.9.

Example 4

The electrosurgical system of Example 2, wherein a ratio of the second area to the first area is less than or equal to about 0.7.

Example 5

The electrosurgical system of Example 2, wherein a ratio of the second area to the first area is less than or equal to about 0.5.

Example 6

The electrosurgical system of any one or more of Example 1 through Example 5, wherein the electrically non-conducting non-stick material has a surface energy value between 1100 mJ/m$^2$ and 5 mJ/m$^2$.

Example 7

The electrosurgical system o of any one or more of Example 1 through Example 5, wherein the electrically non-conducting non-stick material has a surface energy value between 50 mJ/m$^2$ and 40 mJ/m$^2$.

Example 8

The electrosurgical system of any one or more of Example 1 through Example 5, wherein the electrically non-conducting non-stick material has a surface energy value between 40 mJ/m$^2$ and 12 mJ/m$^2$.

Example 9

An end effector for an electrosurgical device, the end effector comprising:
 a first jaw comprising a first energy delivery surface configured to be in electrical communication with a first terminal of an RF current generator; and
 a second jaw comprising a second energy delivery surface configured to be in electrical communication with a second terminal of the RF current generator,
 wherein at least a portion of the first energy delivery surface comprises a patterned coating of an electrically non-conducting non-stick material.

Example 10

The end effector of Example 9, wherein the first energy delivery surface has a first area and the at least portion of the first energy delivery surface comprising the patterned coating has a second area.

Example 11

The end effector of Example 10, wherein a ratio of the second area to the first area is less than or equal to about 0.8.

Example 12

The end effector of Example 10, wherein a ratio of the second area to the first area is less than or equal to about 0.7.

Example 13

The end effector of Example 10, wherein a ratio of the second area to the first area is less than or equal to about 0.5.

Example 14

The electrosurgical system of any one or more of Example 9 through Example 13, wherein the electrically non-conducting non-stick material has a surface energy value between 1100 mJ/m$^2$ and 5 mJ/m$^2$.

Example 15

The electrosurgical system of any one or more of Example 9 through Example 13, wherein the electrically non-conducting non-stick material has a surface energy value between 50 mJ/m$^2$ and 40 mJ/m$^2$.

Example 16

The electrosurgical system of any one or more of Example 9 through Example 13, wherein the electrically non-conducting non-stick material has a surface energy value between 40 mJ/m$^2$ and 12 mJ/m$^2$.

Example 17

The end effector of any one or more of Example 9 through Example 16, wherein the patterned coating comprises the electrically non-conducting non-stick material disposed within one or more recessed features fabricated in the first energy delivery surface.

Example 18

The end effector of any one or more of Example 9 through Example 17, wherein the one or more recessed features comprise one or more circular features.

Example 19

The end effector of any one or more of Example 9 through Example 18, wherein the one or more recessed features comprise one or more rectangular features.

Example 20

The end effector of any one or more of Example 9 through Example 19, wherein the one or more recessed features comprise one or more linear features.

Example 21

The end effector of Example 20, wherein the one or more linear features are disposed along or parallel to a longitudinal axis of the first energy delivery surface.

Example 22

The end effector of Example 20, wherein the one or more linear features are disposed along or parallel to a transverse axis of the first energy delivery surface.

Example 23

The end effector of any one or more of Example 9 through Example 22, wherein the patterned coating comprises the electrically non-conducting non-stick material disposed on and in direct physical communication with an exposed surface of the first energy delivery surface.

Example 24

The end effector of Example 23, wherein the patterned coating comprises a coating of the non-stick material lacking one or more portions of the non-stick material.

Example 25

The end effector of Example 24, wherein the portions of the non-stick material comprise one or more circular portions of the non-stick material.

Example 26

The end effector of any one or more of Example 24 through Example 25, wherein the portions of the non-stick material comprise one or more rectangular portions of the non-stick material.

Example 27

The end effector of any one or more of Example 24 through Example 26, wherein the portions of the non-stick material comprise one or more elongated portions of the non-stick material.

Example 28

The end effector of any one or more of Example 21 through Example 27, wherein at least a portion of the second energy delivery surface comprises a second patterned coating of the electrically non-conducting non-stick material that is disposed on and is in direct physical communication with an exposed surface of the second energy delivery surface; and wherein the patterned coating is spatially offset with respect to the second patterned coating when the first jaw is brought into a proximate position to the second jaw.

Example 29

The end effector of Example 28, wherein the second energy delivery surface has a third area and the at least portion of the second energy delivery surface comprising the second patterned coating has a fourth area.

Example 30

The end effector of Example 29, wherein a ratio of the fourth area to the third area is less than or equal to about 0.8.

Example 31

The end effector of Example 29, wherein a ratio of the fourth area to the third area is less than or equal to about 0.7.

Example 32

The end effector of Example 29, wherein a ratio of the fourth area to the third area is less than or equal to about 0.6.

Example 33

The end effector of any one or more of Example 28 through Example 32, wherein the patterned coating comprises a coating of the non-stick material lacking one or more elongated portions of the non-stick material and the second patterned coating comprises a coating of the non-stick material lacking one or more second elongated portions of the non-stick material.

What is claimed is:
1. An electrosurgical system comprising:
an RF current generator;
a handle body; and
an end effector in mechanical communication with the handle body, the end effector comprising:
a first jaw comprising a first energy delivery surface having a first surface area in electrical communication with a first terminal of the RF current generator; and
a second jaw comprising a second energy delivery surface having a second surface area in electrical communication with a second terminal of the RF current generator,
wherein a first longitudinal portion of the first energy delivery surface comprises a coating of an electrically non-conducting non-stick material,
wherein a second longitudinal portion of the first energy delivery surface comprises an un-coated portion of the first energy delivery surface having a first un-coated area, wherein a first longitudinal portion of the second energy delivery surface comprises a coating of the electrically non-conducting non-stick material, wherein a second longitudinal portion of the second energy delivery surface comprises an un-coated portion of the second energy delivery surface having a second un-coated area, wherein, in a configuration where the first jaw is juxtaposed with the second jaw, a first lengthwise section of the second longitudinal portion of the second energy delivery surface is disposed directly opposite a first lengthwise section of the first longitudinal portion of the first energy delivery surface, wherein, in the configuration where the first jaw is juxtaposed with the second jaw, a second lengthwise section of the second longitudinal portion of the second energy delivery surface is disposed directly opposite a first lengthwise section of the second longitudinal portion of the first energy delivery surface, wherein, in the configuration where the first jaw is juxtaposed with the second jaw, a first lengthwise section of the first longitudinal portion of the second energy delivery surface is disposed directly opposite a second lengthwise section of the second longitudinal portion of the first energy delivery surface, and wherein, in the configuration where the first jaw is juxtaposed with the second jaw, a second lengthwise section of the first longitudinal portion of the second energy delivery surface is disposed directly opposite a second lengthwise section of the first longitudinal portion of the first energy delivery surface.

2. The electrosurgical system of claim 1, wherein the electrically non-conducting non-stick material has a surface energy value between 1100 mJ/m2 and 5 mJ/m2.

3. The electrosurgical system of claim 1, wherein the electrically non-conducting non-stick material has a surface energy value between 50 mJ/m2 and 40 mJ/m2.

4. The electrosurgical system of claim 1, wherein the electrically non-conducting non-stick material has a surface energy value between 40 mJ/m2 and 12 mJ/m2.

5. The electrosurgical system of claim 1, wherein the electrically non-conducting non-stick material comprises a fluoropolymer.

6. An end effector for an electrosurgical device, the end effector comprising:
- a first jaw comprising a first energy delivery surface having a first surface area configured to be in electrical communication with a first terminal of an RF current generator; and
- a second jaw comprising a second energy delivery surface having a second surface area configured to be in electrical communication with a second terminal of the RF current generator, wherein a first longitudinal portion of the first energy delivery surface comprises a coating of an electrically non-conducting non-stick material, wherein a second longitudinal portion of the first energy delivery surface comprises an un-coated portion of the first energy delivery surface having a first un-coated area, wherein a first longitudinal portion of the second energy delivery surface comprises a coating of the electrically non-conducting non-stick material, wherein a second longitudinal portion of the second energy delivery surface comprises an un-coated portion of the second energy delivery surface having a second un-coated area, wherein, in a configuration where the first jaw is juxtaposed with the second jaw, a first lengthwise section of the second longitudinal portion of the second energy delivery surface is disposed directly opposite a first lengthwise section of the first longitudinal portion of the first energy delivery surface, wherein, in the configuration where the first jaw is juxtaposed with the second jaw, a second lengthwise section of the second longitudinal portion of the second energy delivery surface is disposed directly opposite a first lengthwise section of the second longitudinal portion of the first energy delivery surface, wherein, in the configuration where the first jaw is juxtaposed with the second jaw, a first lengthwise section of the first longitudinal portion of the second energy delivery surface is disposed directly opposite a second lengthwise section of the second longitudinal portion of the first energy delivery surface, and wherein, in the configuration where the first jaw is juxtaposed with the second jaw, a second lengthwise section of the first longitudinal portion of the second energy delivery surface is disposed directly opposite a second lengthwise section of the first longitudinal portion of the first energy delivery surface.

7. The end effector of claim 6, wherein the electrically non-conducting non-stick material has a surface energy value between 1100 mJ/m2 and 5 mJ/m2.

8. The end effector of claim 6, wherein the electrically non-conducting non-stick material has a surface energy value between 50 mJ/m2 and 40 mJ/m2.

9. The end effector of claim 6, wherein the electrically non-conducting non-stick material has a surface energy value between 40 mJ/m2 and 12 mJ/m2.

10. The end effector of claim 6, wherein the electrically non-conducting non-stick material comprises a fluoropolymer.

* * * * *